US010676520B2

(12) United States Patent
Kauvar et al.

(10) Patent No.: US 10,676,520 B2
(45) Date of Patent: Jun. 9, 2020

(54) ANTIBODIES USEFUL IN PASSIVE INFLUENZA IMMUNIZATION

(75) Inventors: Lawrence M. Kauvar, San Francisco, CA (US); Stote Ellsworth, Palo Alto, CA (US); William Usinger, Lafayette, CA (US); Krista M. McCutcheon, Burlingame, CA (US); Minha Park, Brisbane, CA (US); Bo Chen, Daly City, CA (US); Ying-Ping Jiang, Lafayette, CA (US)

(73) Assignee: TRELLIS BIOSCIENCE, LLC, Redwood City, CA (US)

( * ) Notice: Subject to any disclaimer, the term of this patent is extended or adjusted under 35 U.S.C. 154(b) by 386 days.

(21) Appl. No.: 13/163,489

(22) Filed: Jun. 17, 2011

(65) Prior Publication Data

US 2012/0020971 A1   Jan. 26, 2012

Related U.S. Application Data

(60) Provisional application No. 61/355,978, filed on Jun. 17, 2010, provisional application No. 61/443,103, filed on Feb. 15, 2011, provisional application No. 61/445,455, filed on Feb. 22, 2011.

(51) Int. Cl.
| | |
|---|---|
| *A61K 39/42* | (2006.01) |
| *C12N 5/10* | (2006.01) |
| *C07K 16/10* | (2006.01) |
| *A61K 39/00* | (2006.01) |

(52) U.S. Cl.
CPC .... *C07K 16/1018* (2013.01); *A61K 2039/505* (2013.01); *C07K 2317/21* (2013.01); *C07K 2317/33* (2013.01); *C07K 2317/34* (2013.01); *C07K 2317/76* (2013.01); *C07K 2317/92* (2013.01)

(58) Field of Classification Search
CPC ............. C07K 2317/76; C07K 14/005; C07K 16/1018; A61K 39/145; A61K 45/06
See application file for complete search history.

(56) References Cited

U.S. PATENT DOCUMENTS

| | | | |
|---|---|---|---|
| 6,235,708 B1 | 5/2001 | Holloway et al. | |
| 7,696,330 B2 | 4/2010 | Meulen et al. | |
| 2003/0100096 A1 | 5/2003 | Holloway | |
| 2009/0311265 A1 | 12/2009 | Van Den Brink et al. | |
| 2010/0086555 A1 | 4/2010 | Lanzavecchia | |
| 2012/0039899 A1* | 2/2012 | Olsen et al. | 424/142.1 |

FOREIGN PATENT DOCUMENTS

| | | |
|---|---|---|
| WO | WO2003080672 | 10/2003 |
| WO | 2004/080403 A2 | 9/2004 |
| WO | 2007134327 A2 | 11/2007 |
| WO | WO-2008/028946 | 3/2008 |
| WO | WO 2009/121004 A2 * | 1/2009 ............ C07K 16/00 |
| WO | WO 2009/079259 A2 * | 6/2009 ............ C07K 16/00 |
| WO | WO-2010/010466 | 1/2010 |
| WO | WO-2010/010467 | 1/2010 |
| WO | 2010022120 A1 | 2/2010 |
| WO | WO-2010/074656 | 7/2010 |
| WO | WO-2011/117848 | 9/2011 |
| WO | WO-2012/045001 | 5/2012 |

OTHER PUBLICATIONS

Steel et al. (MBio, Apr. 2010, vol. 1, p. 1-9).*
Wang et al. (PLoS, Feb. 2010, vol. 6, p. 1-9).*
Usinger et al. (Abstract, Jul. 16-20, 2011, American Society of Virology).*
Corti et al., "A Neutralizing Antibody Selected from Plasma Cells That Binds to Group 1 and Group 2 Influenza A Hemagglutinins", Science (2011) 333:850-856.
Donis et al., "Distinct Lineages of Influenza Virus H4 Hemagglutinin Genes in Different Regions of the World", Virology (1989) 169:408-417.
Ekiert et al., "Antibody Recognition of a Highly Conserved Influenza Virus Epitope", Science (2009) 324:246-251.
Kostolansky et al., "Antibody Response to Hidden Epitope of Influenza A Haemagglutinin Elicited by Anti-Idiotypic Antibodies", Acta vifologica (1994) 38:215-222.
Prabhu et al., "Monoclonal Antibodies against the Fusion Peptide of Hemagglutinin Protect Mice from Lethal Influenza A Virus H5N1 Infection", Journal of Virology (2009) 83(6):2553-2562.
Supplementary European Search Report for EP 11796555.8, dated Oct. 22, 2013, 17 pages.
Ziegler et al., "Type- and Subtype-Specific Detection of Influenza Viruses in Clinical Specimens by Rapid Culture Assay", Journal of Clinical Microbiology (1995) 33(2):318-321.
Abrahamson, M., et al. "Identification of the Probable Inhibitory Reactive Sites of the Cysteine Proteinase Inhibitors Human Cystatin C and Chicken Cystatin." The Journal of Biological Chemistry, 1987, vol. 262, No. 20, pp. 9688-9694.
Bright et al., Cross-clade protective immune responses to influenza viruses with H5N1 HA and NA elicited by an Influenza Virus-Like Particle. Plos ONE, vol. 3 e1501, pp. 1-14.
Kuboto-Koketsu; et al., "Broad neutralizing human monoclonal antibodies against influenza virus from vaccinated healthy donors", Biochem Biophys Res Commun (Sep. 11, 2009), 387(1):180-5.
Song, G., et al. "Progesterone and Interferon Regulate Cystatin C in the Endometrium." Endocrinology, 2006, vol. 147, pp. 3478-3483.
Throsby, M., et al. "Heterosubtypic neutralizing monoclonal antibodies crossprotective against H5N1 and H1 N1 recovered from human IgM+ memory B cells.", PLOS ONE 2008, vol. 3, No. 12, 2008, p. e3942, ISSN: 1932-6203.

(Continued)

*Primary Examiner* — Agnieszka Boesen
(74) *Attorney, Agent, or Firm* — MH2 Technology Law Group, LLP

(57) ABSTRACT

Monoclonal antibodies and fragments thereof that are cross-reactive with multiple clades of influenza virus including both Group 1 and Group 2 representatives are disclosed. These antibodies are useful in controlling influenza epidemics and pandemics as well as in providing prophylactic or therapeutic protection against seasonal influenza.

15 Claims, 9 Drawing Sheets

Specification includes a Sequence Listing.

(56) References Cited

OTHER PUBLICATIONS

Gershoni, Jonathan, M., et al., "Epitope Mapping—The first step in developing epitope-based vaccines", Biodrugs, Adis International Ltd, NZ, vol. 21, No. 3, Jan. 1, 2007, pp. 145-156.
Mei, et al., "Antigen recognition by an antibody light chain", Journal of Biological Chemistry, Jan. 7, 1994. vol. 269, No. 1, pp. 734-738.
Rudikoff, Stuart, et al., "Single amino acid substitution altering antigen-binding specificity", Proc. Natl. Acad. Sci. USA, Mar. 1982, vol. 79, pp. 1979-1983.
Tamura, Midori, et al., "Structural correlates of an anticarcinoma antibody: Identification of specificity-determining residues (SKRs) and development of a minimally immunogenic antibody variant by retention of SDRs only", J Immunol 2000; 164; 1432-1441.
Bianchi, E. et al., Universal Influenza B Vaccine Based on the Maturation Cleavage Site of the Hemagglutinin Precursor, J. Virol. (2005) 79(12):7380-7388.
Australian Office Action issued in Australian Patent Application No. 2011268072 dated Feb. 23, 2016, pp. 1-4.
Australian Office Action issued in Australian Patent Application No. 2017203924 dated Jul. 23, 2018, pp. 1-5.
Australian Office Action issued in Australian Patent Application No. 2017203924 dated Jun. 17, 2019, pp. 1-3.
English-language translation of Brazilian Office Action issued in Brazilian Patent Application No. BR112012032185-4 dated Oct. 31, 2019, pp. 1-4.
Canadian Office Action issued in Canadian Patent Application No. 2,839,421 dated Feb. 10, 2017, pp. 1-6.
Canadian Office Action issued in Canadian Patent Application No. 2,839,421 dated Mar. 16, 2018, pp. 1-6.
English-language translation of Chinese Office Action issued in Chinese Patent Application No. 201180035923.5 dated May 6, 2014, pp. 1-6.
English-language translation of Chinese Office Action issued in Chinese Patent Application No. 201180035923.5 dated Jan. 14, 2015, pp. 1-3.
English-language translation of Chinese Office Action issued in Chinese Patent Application No. 201180035923.5 dated Sep. 30, 2015, pp. 1-3.
English-language translation of Chinese Office Action issued in Chinese Patent Application No. 201610806357.8 dated Dec. 25, 2018, pp. 1-6.
English-language translation of Chinese Office Action issued in Chinese Patent Application No. 201610806357.8 dated Sep. 17, 2019, pp. 1-6.
International Search Report issued in International PCT Application No. PCT/US2011/40982 dated Nov. 25, 2011, pp. 1-8.
Communication from the European Patent Office issued in European Patent Application No. 11 796 555.8 dated Sep. 1, 2015, pp. 1-12.
Communication from the European Patent Office issued in European Patent Application No. 11 796 555.8 dated May 6, 2016, pp. 1-13.
Communication from the European Patent Office issued in European Patent Application No. 11 796 555.8 dated Apr. 13, 2017, pp. 1-8.
English-language translation of Israeli Office Action issued in Israeli Patent Application No. 223666 dated Jul. 15, 2015, pp. 1-7.
English-language translation of Israeli Office Action issued in Israeli Patent Application No. 223666 dated Mar. 22, 2017, pp. 1-5.
English-language translation of Israeli Office Action issued in Israeli Patent Application No. 223666 dated Dec. 26, 2018, pp. 1-4.
English-language translation of Japanese Office Action issued in Japanese Patent Application No. 2013-557080 dated Jun. 7, 2016, pp. 1-3.
English-language translation of Korean Office Action issued in Korean Patent Application No. 10-2013-7001292 dated Jun. 19, 2017, pp. 1-7.
English-language translation of Russian Office Action issued in Russian Patent Application No. 2013102073 (002738) dated Jul. 28, 2016, pp. 1-7.
Huang, Yaojiang et al., "Principles and Applications of Protein Engineering," Central University of Nationalities Press, Edition 1, pp. 248-249, published on Aug. 31, 2007 (English-language translation).
Yu, Boyang, "Biotechnology of Traditional Chinese Medicine," China Medical Science and Technology Press, Edition 1, p. 409, published on Dec. 31, 2005 (English-language translation).

* cited by examiner

C

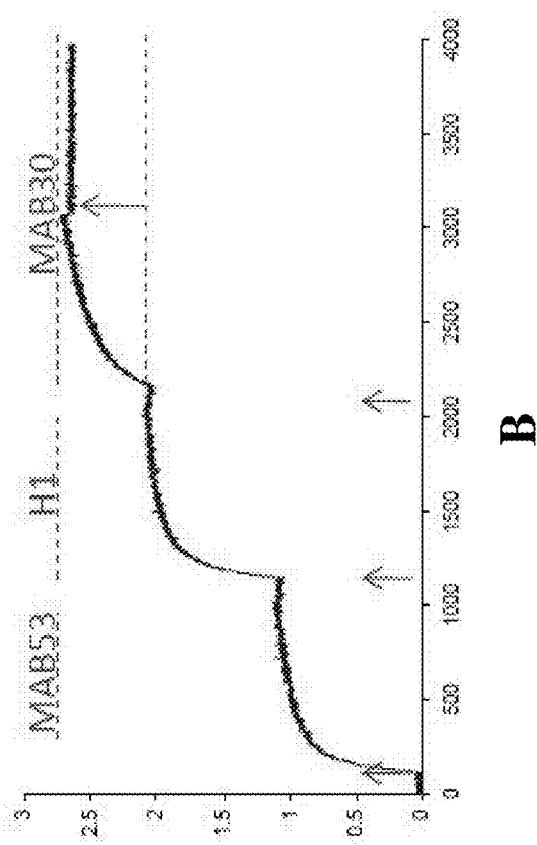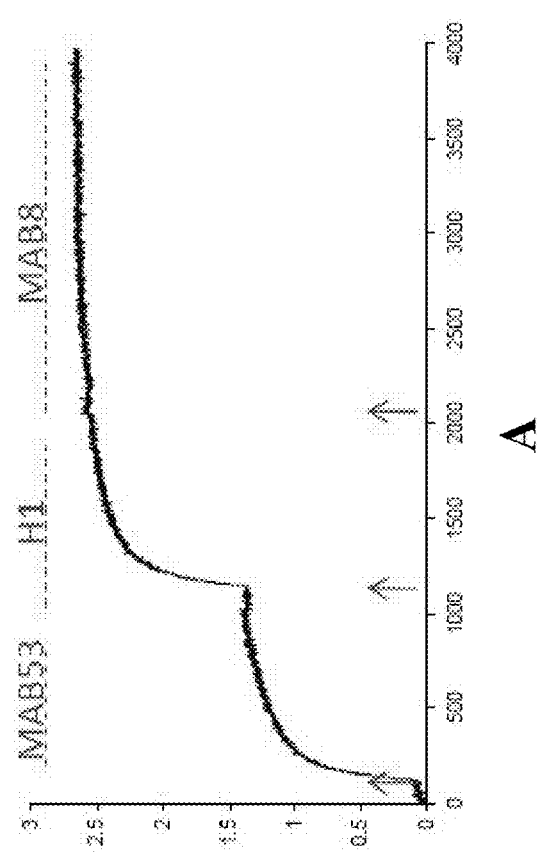
Figure 4

VH

Kabat No. 1 2 3 4 5 6 7 8 9 10 11 12 13 14 15 16 17 18 19 20 21 22 23 24 25 26 27 28 29 30 31 32 33 34 35 A B 36 37 38 39 40 41 42 43 44

IGHV1-69*01  Q V Q L V Q S G A E V R K P G S S V K V S C K V S G G I I R K Y A I N . . W V R Q A P G Q G

Kabat - CDR H1

45 46 47 48 49 50 51 52 A B C 53 54 55 56 57 58 59 60 61 62 63 64 65 66 67 68 69 70 71 72 73 74 75 76 77 78 79 80 81 82 A B C 83 84

L E W M G G I I A . . I F N T A N Y A Q K F Q G R V T I T A D E S T S T V Y M E L S S L R S

Kabat - CDR H2

85 86 87 88 89 90 91 92 93 94 95 96 97 98 99 100 A B C D E F G H I J K 101 102 103 104 105 106 107 108 109 110 111 112 113

E D T A L Y Y C A R G M N Y Y S D Y . . . . . F D Y W G Q G S L V T V S P

Kabat - CDR H3

A

VL

Kabat No. 1 2 3 4 5 6 7 8 9 10 11 12 13 14 15 16 17 18 19 20 21 22 23 24 25 26 27 A B C D E F 28 29 30 31 32 33 34 35 36

IGKV3-20*01  E I V L T Q S P G T L S L S P G E R A T L S C R A S Q S . . . . . V R S N N L A W Y

Kabat - CDR L1

37 38 39 40 41 42 43 44 45 46 47 48 49 50 51 52 53 54 A B C D E 55 56 57 58 59 60 61 62 63 64 65 66 67 68 69 70 71

Q H K P G Q A P R L L I F G A S S R . . . A T G I P D R F S G S G S G T D F

Kabat - CDR L2

72 73 74 75 76 77 78 79 80 81 82 83 84 85 86 87 88 89 90 91 92 93 94 95 A B C D E F 96 97 98 99 100 101 102 103 104 105 106 107

T L T I S R L E P E D F A V Y Y C Q Q Y G S S P A . . . L T F G G G T K V E I K

Kabat - CDR L3

SEQUENCE LISTING

```
<160> NUMBER OF SEQ ID NOS: 84

<210> SEQ ID NO 1
<211> LENGTH: 8
<212> TYPE: PRT
<213> ORGANISM: Artificial Sequence
<220> FEATURE:
<223> OTHER INFORMATION: synthetically constructed A/H3/HA0 consensus
      sequence

<400> SEQUENCE: 1

Asn Val Pro Glu Lys Gln Thr Arg
1               5

<210> SEQ ID NO 2
<211> LENGTH: 11
<212> TYPE: PRT
<213> ORGANISM: Artificial Sequence
<220> FEATURE:
<223> OTHER INFORMATION: synthetically constructed A/H3/HA0 consensus
      sequence

<400> SEQUENCE: 2

Gly Ile Phe Gly Ala Ile Ala Gly Phe Ile Glu
1               5                   10
```

<210> SEQ ID NO 3
<211> LENGTH: 8
<212> TYPE: PRT
<213> ORGANISM: Artificial Sequence
<220> FEATURE:
<223> OTHER INFORMATION: synthetically constructed A/H1/HA0 consensus
      sequence

<400> SEQUENCE: 3

Asn Ile Pro Ser Ile Gln Ser Arg
1               5

<210> SEQ ID NO 4
<211> LENGTH: 11
<212> TYPE: PRT
<213> ORGANISM: Artificial Sequence
<220> FEATURE:
<223> OTHER INFORMATION: synthetically constructed A/H1/HA0 consensus
      sequence

<400> SEQUENCE: 4

Gly Leu Phe Gly Ala Ile Ala Gly Phe Ile Glu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: synthetically constructed B/HA0 consensus
      sequence

<400> SEQUENCE: 5

Pro Ala Lys Leu Leu Lys Glu Arg
1               5

<210> SEQ ID NO 6
<211> LENGTH: 11
<212> TYPE: PRT
<213> ORGANISM: Artificial Sequence
<220> FEATURE:
<223> OTHER INFORMATION: synthetically constructed B/HA0 consensus
      sequence

<400> SEQUENCE: 6

Gly Phe Phe Gly Ala Ile Ala Gly Phe Leu Glu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetically constructed consensus sequence

<400> SEQUENCE: 7

Arg Gly Ile Leu Phe Phe Gly Ala Ile Ala Gly Phe Leu Glu
1               5                   10

<210> SEQ ID NO 8
<211> LENGTH: 330
<212> TYPE: PRT
<213> ORGANISM: Homo sapiens
<220> FEATURE:
<221> NAME/KEY: CHAIN
<222> LOCATION: (1)...(330)
<223> OTHER INFORMATION: IgG1 heavy chain amino acid sequence of constant region

<400> SEQUENCE: 8

Ala Ser Thr Lys Gly Pro Ser Val Phe Pro Leu Val Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 121
<212> TYPE: PRT
<213> ORGANISM: Artificial Sequence
<220> FEATURE:
<223> OTHER INFORMATION: synthetically constructed MAB1 heavy chain
      amino acid sequence of variable domain

<400> SEQUENCE: 9

Gln Val Gln Leu Gln Glu Ser Gly Pro Gly Leu Val Lys Pro Ser Glu

```
                1               5                  10                  15
            Thr Leu Ser Leu Ile Cys Arg Val Ser Gly Gly Ser Ile Ser Ser His
                        20                  25                  30
            Tyr Trp Ser Trp Ile Arg Gln Pro Gly Lys Gly Leu Glu Trp Ile
                        35                  40                  45
            Gly Tyr Ile Ser Tyr Arg Gly Arg Ser Asn His Asn Pro Ser Leu Gly
                    50                  55                  60
            Arg Arg Val Ser Met Ser Ile Asp Thr Ser Glu Asn Gln Phe Ser Leu
            65                  70                  75                  80
            Asn Leu Ser Ser Val Ile Ala Ala Asp Thr Ala Val Tyr Tyr Cys Ala
                            85                  90                  95
            Arg Asp Ala Thr Gly Ile Arg Glu Ile Asn Ala Leu Asp Ile Trp Gly
                            100                 105                 110
            Gln Gly Thr Thr Val Thr Val Ser Ser
                    115                 120
```

<210> SEQ ID NO 10
<211> LENGTH: 121
<212> TYPE: PRT
<213> ORGANISM: Artificial Sequence
<220> FEATURE:
<223> OTHER INFORMATION: synthetically constructed MAB8 heavy chain
      amino acid sequence of variable domain

<400> SEQUENCE: 10

```
            Glu Val Gln Leu Val Glu Ser Gly Gly Gly Leu Val Lys Pro Gly Gly
            1               5                   10                  15
            Ser Leu Arg Leu Ser Cys Ala Ala Ser Gly Phe Thr Phe Ser Thr Tyr
                        20                  25                  30
            Thr Met Ser Trp Val Arg Gln Ala Pro Gly Gln Gly Leu Glu Trp Val
                        35                  40                  45
            Ser Ser Ile Thr Arg Thr Ser Ser Asn Ile Tyr Tyr Ala Asp Ser Val
                    50                  55                  60
            Glu Gly Arg Phe Thr Ile Ser Arg Asp Asn Ala Lys Asn Ser Leu Tyr
            65                  70                  75                  80
            Leu Gln Met His Ser Leu Arg Val Glu Asp Thr Ala Val Tyr Tyr Cys
                            85                  90                  95
            Ala Arg Ile Ser Gly Val Val Gly Pro Val Pro Phe Asp Tyr Trp Gly
                            100                 105                 110
            Gln Gly Thr Leu Ile Thr Val Ser Ser
                    115                 120
```

<210> SEQ ID NO 11
<211> LENGTH: 118
<212> TYPE: PRT
<213> ORGANISM: Artificial Sequence
<220> FEATURE:
<223> OTHER INFORMATION: synthetically constructed MAB30 heavy chain
      amino acid sequence of variable domain

<400> SEQUENCE: 11

```
            Glu Val Gln Leu Val Glu Ser Gly Gly Gly Leu Val Gln Pro Gly Gly
            1               5                   10                  15
            Ser Leu Arg Leu Ser Cys Ala Ala Ser Gly Phe Thr Phe Ser Asp His
                        20                  25                  30
            Tyr Met Asp Trp Val Arg Gln Ala Pro Gly Lys Gly Leu Glu Trp Val
                        35                  40                  45
            Gly Arg Ile Arg Asn Lys Ala Ala Ile Tyr Thr Thr Glu Tyr Ala Ala
```

```
                  50                  55                  60
Ser Val Lys Gly Arg Phe Thr Ile Ser Arg Asp Asp Leu Lys Ser Ser
 65                  70                  75                  80

Val Tyr Leu Gln Met Asn Ser Leu Lys Thr Asp Asp Thr Ala Ile Tyr
                 85                  90                  95

Tyr Cys Ala Arg Ser Tyr Gly Tyr Phe Asp Tyr Trp Gly Gln Gly Thr
                100                 105                 110

Leu Val Thr Val Ser Ser
            115

<210> SEQ ID NO 12
<211> LENGTH: 119
<212> TYPE: PRT
<213> ORGANISM: Artificial Sequence
<220> FEATURE:
<223> OTHER INFORMATION: synthetically constructed MAB42 heavy chain
      amino acid sequence of variable domain

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Asn Gly Tyr
                20                  25                  30

Tyr Met His Trp Val Arg Gln Ala Pro Gly Gln Gly Leu Glu Trp Met
            35                  40                  45

Gly Trp Ile Asn Leu Ser Ser Gly Gly Thr Asp Tyr Ala Gln Lys Phe
     50                  55                  60

Gln Gly Trp Val Thr Leu Thr Arg Asp Thr Ser Ile Thr Thr Ala Tyr
 65                  70                  75                  80

Met Glu Leu Ser Ser Leu Arg Ser Asn Asp Thr Ala Val Tyr Tyr Cys
                 85                  90                  95

Ala Arg Ile Arg Pro Arg Thr Gly Gly Leu Asp Ser Trp Gly Gln Gly
                100                 105                 110

Thr Leu Val Ile Val Ser Ser
            115

<210> SEQ ID NO 13
<211> LENGTH: 121
<212> TYPE: PRT
<213> ORGANISM: Artificial Sequence
<220> FEATURE:
<223> OTHER INFORMATION: synthetically constructed MAB48 heavy chain
      amino acid sequence of variable domain

<400> SEQUENCE: 13

Gln Val Gln Leu Val Gln Ser Gly Ala Glu Val Lys Lys Pro Gly Ser
 1               5                  10                  15

Ser Val Lys Val Ser Cys Lys Ala Ser Gly Val Thr Phe Thr Ala Tyr
                20                  25                  30

Ala Ile Ser Trp Val Arg Gln Ala Pro Gly Arg Gly Leu Glu Trp Met
            35                  40                  45

Gly Gly Ile Ser Pro Leu Phe Gly Ile Val Asn Phe Gly Gln Asn Phe
     50                  55                  60

Gln Gly Arg Val Thr Ile Thr Ala Asp Lys Ser Thr Gly Ala Ala Tyr
 65                  70                  75                  80

Met Glu Leu Ser Ser Leu Ser Ser Glu Asp Thr Ala Met Tyr Tyr Cys
                 85                  90                  95

Ala Arg Gly Pro Tyr Tyr Tyr Asp Arg Ser His Leu Asp Tyr Trp Gly
```

```
                    100                 105                 110
Gln Gly Thr Leu Val Thr Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: synthetically constructed MAB49 heavy chain
      amino acid sequence of variable domain

<400> SEQUENCE: 14

Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Thr Ser Leu Arg Ser Asp Asp Thr Ala Met Tyr Tyr Cys
                85                  90                  95

Ala Arg Asp Arg Asn Tyr Tyr Ala Ser Gly Tyr Thr Tyr Asp His Trp Gly
            100                 105                 110

Gln Gly Thr Leu Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: synthetically constructed MAB52 heavy chain
      amino acid sequence of variable domain

<400> SEQUENCE: 15

Gln Val Leu Leu Val Gln Ser Gly Ala Glu Val Lys Lys Pro Gly Ser
1               5                   10                  15

Ser Val Asn Ile Ser Cys Lys Ala Ser Gly Gly Thr Phe Ser Asn Tyr
            20                  25                  30

Ala Ile Ser Trp Val Arg Gln Ala Pro Gly Gln Gly Leu Asp Trp Met
        35                  40                  45

Gly Arg Ile Ile Pro Ile Phe Gly Thr Ala Asn Tyr Ala Gln Lys Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Ile Thr Lys Pro Gly Ser Val Tyr Ala Leu Asp Val Trp Gly Gln
            100                 105                 110

Gly Thr Thr Val Thr Val Ser Ser
        115                 120

<210> SEQ ID NO 16
<211> LENGTH: 120
<212> TYPE: PRT
```

<213> ORGANISM: Artificial Sequence
<220> FEATURE:
<223> OTHER INFORMATION: synthetically constructed MAB53 heavy chain
    amino acid sequence of variable domain

<400> SEQUENCE: 16

```
Gln Val Gln Leu Val Gln Ser Gly Ala Glu Val Arg Lys Pro Gly Ser
1               5                  10                  15

Ser Val Lys Val Ser Cys Lys Val Ser Gly Gly Ile Ile Arg Lys Tyr
            20                  25                  30

Ala Ile Asn Trp Val Arg Gln Ala Pro Gly Gln Gly Leu Glu Trp Met
        35                  40                  45

Gly Gly Ile Ile Ala Ile Phe Asn Thr Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Leu Tyr Tyr Cys
                85                  90                  95

Ala Arg Gly Met Asn Tyr Tyr Ser Asp Tyr Phe Asp Tyr Trp Gly Gln
            100                 105                 110

Gly Ser Leu Val Thr Val Ser Pro
        115                 120
```

<210> SEQ ID NO 17
<211> LENGTH: 120
<212> TYPE: PRT
<213> ORGANISM: Artificial Sequence
<220> FEATURE:
<223> OTHER INFORMATION: synthetically constructed MAB285 heavy chain
    amino acid sequence of variable domain

<400> SEQUENCE: 17

```
Gln Val Gln Leu Val Gln Ser Gly Ala Glu Val Lys Lys Pro Gly Ala
1               5                  10                  15

Ser Val Lys Val Ser Cys Arg Ala Ser Gly Tyr Thr Phe Thr Gly Tyr
            20                  25                  30

Tyr Met Gln Trp Val Arg Gln Ala Pro Gly Gln Gly Leu Glu Trp Met
        35                  40                  45

Gly Phe Ile Asn Ala Asn Thr Gly Val Thr Asn Phe Ala Gln Lys Phe
    50                  55                  60

Gln Gly Arg Val Thr Leu Thr Arg Asp Thr Ser Ile Ser Thr Ala Tyr
65                  70                  75                  80

Met Glu Leu Arg Arg Leu Thr Ser Ala Asp Thr Ala Val Tyr Tyr Cys
                85                  90                  95

Ala Arg Ala Pro Gln Trp Leu Ser Tyr Ser Phe Asp Ile Trp Gly Gln
            100                 105                 110

Gly Thr Met Val Thr Val Ser Ser
        115                 120
```

<210> SEQ ID NO 18
<211> LENGTH: 123
<212> TYPE: PRT
<213> ORGANISM: Artificial Sequence
<220> FEATURE:
<223> OTHER INFORMATION: synthetically constructed MAB321 heavy chain
    amino acid sequence of variable domain

<400> SEQUENCE: 18

```
Glu Val Gln Leu Val Glu Ser Gly Ala Glu Val Arg Ser Pro Gly Ala
1               5                  10                  15
```

```
Ser Val Lys Leu Ser Cys Lys Ala Ser Ala Tyr Thr Phe Ile Asn Tyr
            20                  25                  30

Tyr Leu His Trp Val Arg Gln Ala Pro Gly Gln Arg Leu Glu Trp Met
        35                  40                  45

Gly Trp Ile Asn Pro Asp Ser Gly Val Thr Glu Tyr Ala Gln Thr Phe
50                  55                  60

Gln Gly Arg Val Thr Met Thr Arg Asp Thr Ser Ile Asn Thr Ala Tyr
65                  70                  75                  80

Leu Asp Leu Glu Arg Leu Thr Ser Asp Thr Ala Val Tyr Tyr Cys
            85                  90                  95

Ala Arg Gly Phe Ile Pro Trp Gly Gly Lys Tyr Phe Tyr Leu Asp Tyr
                100                 105                 110

Trp Gly Gln Gly Thr Leu Val Thr Val Ser Ser
            115                 120

<210> SEQ ID NO 19
<211> LENGTH: 127
<212> TYPE: PRT
<213> ORGANISM: Artificial Sequence
<220> FEATURE:
<223> OTHER INFORMATION: synthetically constructed MAB322 heavy chain
      amino acid sequence of variable domain

<400> SEQUENCE: 19

Gln Val Gln Leu Gln Gln Ser Gly Pro Gly Leu Val Lys Pro Ser Gln
1               5                   10                  15

Thr Leu Ser Leu Thr Cys Ser Val Ser Gly Ser Phe Ile Arg Ser Gly
            20                  25                  30

Asp Tyr Asn Trp Ser Trp Ile Arg Gln Pro Pro Gly Lys Gly Leu Glu
        35                  40                  45

Trp Ile Gly Tyr Ile Asp Asn Ser Gly Ser Thr His Tyr Asn Pro Ser
50                  55                  60

Leu Lys Ser Arg Val Ser Ile Ser Val Asp Thr Ser Lys Asn His Leu
65                  70                  75                  80

Ser Leu Lys Leu Ser Phe Val Thr Asp Ala Asp Thr Gly Val Tyr Tyr
            85                  90                  95

Cys Ala Gly Glu Gln Ala Ser Asp Ser Arg Gly Asn Tyr Tyr Tyr Tyr
                100                 105                 110

Ala Met Asp Val Trp Gly Gln Gly Thr Pro Val Thr Val Ser Ser
            115                 120                 125

<210> SEQ ID NO 20
<211> LENGTH: 120
<212> TYPE: PRT
<213> ORGANISM: Artificial Sequence
<220> FEATURE:
<223> OTHER INFORMATION: synthetically constructed MAB375 heavy chain
      amino acid sequence of variable domain

<400> SEQUENCE: 20

Gln Val Gln Leu Gln Gln Ser Gly Pro Gly Leu Met Lys Pro Ser Glu
1               5                   10                  15

Thr Leu Ser Leu Ser Cys Thr Val Ser Gly Asp Ser Val Ser Ser Phe
            20                  25                  30

Tyr Trp Ser Trp Ile Arg Gln Ser Pro Gly Lys Gly Leu Glu Trp Ile
        35                  40                  45

Gly Tyr Leu Leu Tyr Ser Gly Asn Thr Lys Tyr Asn Pro Ser Leu Lys
50                  55                  60
```

```
Ser Arg Ala Thr Ile Ser Arg Asp Thr Ser Lys Asn Gln Leu Ser Leu
 65                  70                  75                  80

Glu Leu Thr Ser Leu Thr Ala Ala Asp Thr Ala Val Tyr Tyr Cys Ala
                 85                  90                  95

Arg Val Val Arg Trp Arg His Gly Gly Asp Leu Asp Val Trp Gly Gln
            100                 105                 110

Gly Thr Met Val Thr Val Ser Ser
        115                 120

<210> SEQ ID NO 21
<211> LENGTH: 126
<212> TYPE: PRT
<213> ORGANISM: Artificial Sequence
<220> FEATURE:
<223> OTHER INFORMATION: synthetically constructed MAB376 heavy chain
      amino acid sequence of variable domain

<400> SEQUENCE: 21

Gln Val Gln Leu Val Gln Ser Gly Gly Asp Leu Val Gln Pro Gly Gly
 1               5                  10                  15

Ser Leu Arg Leu Ser Cys Ala Val Ser Gly Phe Ile Phe Arg Lys Tyr
            20                  25                  30

Ile Met Ser Trp Val Arg Gln Ala Pro Gly Lys Gly Pro Glu Trp Val
        35                  40                  45

Ala Val Ile Ser Ser Ser Gly Asp Arg Thr Phe Tyr Ala Asp Ser Val
    50                  55                  60

Glu Gly Arg Phe Ile Val Ser Arg Asp Asn Ser Lys Asp Thr Leu Phe
 65                  70                  75                  80

Leu Gln Met Asn Ser Leu Arg Thr Glu Asp Thr Ala Met Tyr Tyr Cys
                 85                  90                  95

Ala Lys Asp Leu Leu Gly Phe Cys Ser Gly Gly Asp Cys Leu Lys Val
            100                 105                 110

Phe Asp Leu Trp Gly Arg Gly Thr Met Val Thr Val Ser Ser
        115                 120                 125

<210> SEQ ID NO 22
<211> LENGTH: 120
<212> TYPE: PRT
<213> ORGANISM: Artificial Sequence
<220> FEATURE:
<223> OTHER INFORMATION: synthetically constructed MAB377 heavy chain
      amino acid sequence of variable domain

<400> SEQUENCE: 22

Gln Val Gln Leu Leu Gln Ser Gly Pro Gly Leu Ile Lys Ala Ser Glu
 1               5                  10                  15

Thr Leu Ser Leu Ser Cys Ser Val Ser Asn Asp Ser Val Ser Asn Tyr
            20                  25                  30

Tyr Trp Ser Trp Ile Arg Gln Ser Pro Glu Lys Gly Leu Glu Trp Ile
        35                  40                  45

Gly Tyr Leu Leu Tyr Ser Gly Asn Thr Lys Tyr Asn Pro Ser Leu Lys
    50                  55                  60

Ser Arg Ala Ile Ile Ser Arg Asp Met Ser Lys Asn Gln Leu Ser Leu
 65                  70                  75                  80

Arg Val Thr Ser Val Thr Ala Ala Asp Thr Ala Ile Tyr Tyr Cys Ala
                 85                  90                  95

Arg Val Val Arg Trp Arg Phe Gly Gly Asp Met Asp Val Trp Gly Gln
            100                 105                 110
```

```
Gly Thr Ala Val Thr Val Ser Thr
        115                 120
```

<210> SEQ ID NO 23
<211> LENGTH: 120
<212> TYPE: PRT
<213> ORGANISM: Artificial Sequence
<220> FEATURE:
<223> OTHER INFORMATION: synthetically constructed MAB378 heavy chain
      amino acid sequence of variable domain

<400> SEQUENCE: 23

```
Gln Val Gln Leu Gln Gln Ser Gly Pro Gly Leu Ile Lys Pro Ser Glu
1               5                   10                  15

Thr Leu Ser Leu Ser Cys Ser Val Ser Gly Asp Ser Val Asn Asn Tyr
            20                  25                  30

Tyr Trp Ser Trp Ile Arg Gln Pro Pro Glu Lys Gly Leu Glu Trp Ile
        35                  40                  45

Gly Tyr Leu Gln Tyr Ser Gly Ser Thr Lys Tyr Asn Pro Ser Leu Lys
    50                  55                  60

Ser Arg Val Thr Ile Ser Arg Asp Thr Ser Lys Asn Gln Leu Ser Leu
65                  70                  75                  80

Lys Leu Thr Ser Val Thr Ala Ala Asp Thr Ala Ile Tyr Tyr Cys Ala
                85                  90                  95

Arg Val Val Arg Trp Arg His Gly Gly Asp Met Asp Val Trp Gly Gln
            100                 105                 110

Gly Thr Ala Val Thr Val Ser Ser
        115                 120
```

<210> SEQ ID NO 24
<211> LENGTH: 107
<212> TYPE: PRT
<213> ORGANISM: Homo sapiens
<220> FEATURE:
<221> NAME/KEY: CHAIN
<222> LOCATION: (1)...(107)
<223> OTHER INFORMATION: light chain amino acid sequence of constant
      kappa region

<400> SEQUENCE: 24

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 25
<211> LENGTH: 106
<212> TYPE: PRT
<213> ORGANISM: Homo sapiens
<220> FEATURE:

<221> NAME/KEY: CHAIN
<222> LOCATION: (1)...(106)
<223> OTHER INFORMATION: light chain amino acid sequence of constant lambda region

<400> SEQUENCE: 25

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Val Pro Ala Glu Cys Ser
            100                 105

<210> SEQ ID NO 26
<211> LENGTH: 214
<212> TYPE: PRT
<213> ORGANISM: Artificial Sequence
<220> FEATURE:
<223> OTHER INFORMATION: synthetically constructed MAB1 light chain amino acid sequence

<400> SEQUENCE: 26

Asp Ile Gln Met Thr Gln Ser Pro Ser Ser Leu Ser Ala Ser Gly Gly
1               5                   10                  15

Asp Arg Val Thr Ile Thr Cys Arg Ala Ser Gln Ser Val Ser Thr Tyr
            20                  25                  30

Leu Asn Trp Tyr Gln Gln Lys Pro Gly Lys Ala Pro Asn Leu Leu Val
        35                  40                  45

Tyr Ala Val Ser Asn Leu Gln Arg Gly Val Pro Ser Arg Phe Ser Gly
50                  55                  60

Ser Gly Ser Gly Thr His Phe Thr Leu Thr Ile Ser Ser Leu Gln Pro
65                  70                  75                  80

Glu Asp Phe Ala Thr Tyr Tyr Cys Gln Gln Ser Tyr Ser Asp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys

<210> SEQ ID NO 27
<211> LENGTH: 215
<212> TYPE: PRT
<213> ORGANISM: Artificial Sequence
<220> FEATURE:
<223> OTHER INFORMATION: synthetically constructed MAB8 light chain
      amino acid sequence

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Lys Tyr
            20                  25                  30

Leu Asn Trp Tyr Gln Gln Lys Pro Gly Arg Ala Pro Lys Leu Leu Ile
        35                  40                  45

Tyr Ser Ala Ser Ser Leu Gln Ser Gly Val Pro Ser Arg Phe Thr Gly
    50                  55                  60

Ser Gly Ser Gly Thr Asp Phe Thr Leu Thr Ile Ser Leu Gln Pro
65                  70                  75                  80

Glu Asp Phe Ala Thr Tyr Tyr Cys Gln Gln Ser Tyr Arg Pro Ser Gln
                85                  90                  95

Ile Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 28
<211> LENGTH: 214
<212> TYPE: PRT
<213> ORGANISM: Artificial Sequence
<220> FEATURE:
<223> OTHER INFORMATION: synthetically constructed MAB30 light chain
      amino acid sequence

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Asn Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro

```
              65                  70                  75                  80
Asp Asp Phe Ala Thr Tyr Tyr Cys Gln Gln Tyr Asp Thr Tyr Ser Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 29
<211> LENGTH: 216
<212> TYPE: PRT
<213> ORGANISM: Artificial Sequence
<220> FEATURE:
<223> OTHER INFORMATION: synthetically constructed MAB42 light chain
      amino acid sequence

<400> SEQUENCE: 29

Gln Ser Ala Leu Thr Gln Pro Ala Ser Val Ser Gly Ser Ala Gly Gln
1               5                   10                  15

Ser Ile Thr Ile Ser Cys Thr Gly Thr Ser Ser Asp Val Gly Ala Tyr
                20                  25                  30

Asn Phe Val Ser Trp Tyr Gln His His Pro Gly Lys Ala Pro Lys Leu
            35                  40                  45

Met Ile Tyr Asp Val Asp Asn Arg Pro Ser Gly Val Ser Asn Arg Phe
        50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Ser Ser Tyr Arg Arg Asn
                85                  90                  95

Gly Pro Trp Val Phe Gly Gly Gly Thr Lys Leu Thr Val Leu Gly Gln
                100                 105                 110

Pro Lys Ala Ala Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205
```

```
Thr Val Val Pro Ala Glu Cys Ser
    210             215
```

<210> SEQ ID NO 30
<211> LENGTH: 215
<212> TYPE: PRT
<213> ORGANISM: Artificial Sequence
<220> FEATURE:
<223> OTHER INFORMATION: synthetically constructed MAB48 light chain
      amino acid

<400> SEQUENCE: 30

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Asp Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210             215
```

<210> SEQ ID NO 31
<211> LENGTH: 214
<212> TYPE: PRT
<213> ORGANISM: Artificial Sequence
<220> FEATURE:
<223> OTHER INFORMATION: synthetically constructed MAB49 light chain
      amino acid

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Gly Gly
50                  55                  60
```

```
Ser Gly Ser Gly Thr Asp Phe Thr Leu Thr Ile Ser Ser Leu Gln Pro
 65                  70                  75                  80

Glu Asp Phe Ala Leu Tyr Tyr Cys Gln Gln Thr Tyr Ser Ile Pro Ile
                 85                  90                  95

Thr Phe Gly Gln Gly Thr Arg Leu Asp Phe Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 32
<211> LENGTH: 215
<212> TYPE: PRT
<213> ORGANISM: Artificial Sequence
<220> FEATURE:
<223> OTHER INFORMATION: synthetically constructed MAB52 light chain
      amino acid

<400> SEQUENCE: 32

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Thr Ile Ser Thr Tyr
                 20                  25                  30

Leu Asn Trp Tyr Gln Gln Lys Pro Gly Lys Ala Pro Asn Leu Leu Ile
             35                  40                  45

Tyr Thr Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Ala Pro Thr
                 85                  90                  95

Trp Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205
```

Ser Phe Asn Arg Gly Glu Cys
    210                 215

<210> SEQ ID NO 33
<211> LENGTH: 216
<212> TYPE: PRT
<213> ORGANISM: Artificial Sequence
<220> FEATURE:
<223> OTHER INFORMATION: synthetically constructed MAB53 light chain
      amino acid

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Asn Leu Ala Trp Tyr Gln His Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 34
<211> LENGTH: 216
<212> TYPE: PRT
<213> ORGANISM: Artificial Sequence
<220> FEATURE:
<223> OTHER INFORMATION: synthetically constructed MAB285 light chain
      amino acid

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Arg Leu Leu
        35                  40                  45

Ile Tyr Ser Asn Asn Gln Arg Pro Ser Gly Val Pro Asp Arg Phe Ser
    50                  55                  60

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Thr Ser Trp Asp Asp Ser Leu
                 85                  90                  95

Asn Ala Trp Val Phe Gly Gly Thr Arg Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Val Pro Ala Glu Cys Ser
    210                 215

<210> SEQ ID NO 35
<211> LENGTH: 213
<212> TYPE: PRT
<213> ORGANISM: Artificial Sequence
<220> FEATURE:
<223> OTHER INFORMATION: synthetically constructed MAB321 light chain
      amino acid

<400> SEQUENCE: 35

Asp Ile Val Leu Thr Gln Ser Pro Pro Ser Leu Ser Ala Ser Val Gly
 1               5                  10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Asn Ala Pro Arg Ile Leu Ile
        35                  40                  45

Tyr Gly Ala Ser Ser Leu Val Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Pro Leu Tyr
                 85                  90                  95

Thr Phe Gly Pro Gly Thr Gln Leu Asp Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 36
<211> LENGTH: 213
<212> TYPE: PRT
<213> ORGANISM: Artificial Sequence
<220> FEATURE:
<223> OTHER INFORMATION: synthetically constructed MAB322 light chain
      amino acid

<400> SEQUENCE: 36

Asp Ile Val Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Ala Tyr
            20                  25                  30

Leu Asn Trp Tyr Gln His Thr Pro Gly Arg Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Val Thr Tyr Tyr Cys Gln Gln Thr Tyr Asn Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 37
<211> LENGTH: 214
<212> TYPE: PRT
<213> ORGANISM: Artificial Sequence
<220> FEATURE:
<223> OTHER INFORMATION: synthetically constructed MAB375 light chain
      amino acid

<400> SEQUENCE: 37

Asp Ile Gln Met Thr Gln Ser Pro Ser Phe Leu Ser Ala Ser Val Gly
1               5                   10                  15

Asp Arg Val Thr Phe Thr Cys Arg Ala Ser Gln Gly Ile Ala Ser Ser
            20                  25                  30

Leu Ala Trp Tyr Gln Gln Lys Ala Gly Lys Ala Pro Lys Leu Leu Ile
        35                  40                  45

Tyr Ala Ala Ser Thr Leu Glu Asp Gly Val Pro Ser Arg Phe Ser Gly

```
            50                  55                  60
Ser Gly Phe Gly Thr Glu Phe Thr Leu Thr Ile Thr Ser Leu Gln Pro
 65                  70                  75                  80

Glu Asp Phe Ala Thr Tyr Tyr Cys His Gln Val Asn Ser Tyr Pro Arg
                 85                  90                  95

Thr Phe Gly Pro Gly Thr Thr Val Asp Ile Asn Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 214
<212> TYPE: PRT
<213> ORGANISM: Artificial Sequence
<220> FEATURE:
<223> OTHER INFORMATION: synthetically constructed MAB376 light chain
      amino acid

<400> SEQUENCE: 38

Asp Ile Gln Met Thr Gln Ser Pro Ser Thr Leu Ser Ala Ser Val Gly
 1               5                  10                  15

Asp Thr Val Thr Ile Thr Cys Arg Ala Ser Gln Ser Ile Ser Thr Trp
             20                  25                  30

Leu Ala Trp Phe Gln Gln Lys Pro Gly Arg Ala Pro Lys Leu Leu Ile
         35                  40                  45

Tyr Gln Ala Ser Ser Leu Glu Gly Gly Val Pro Ser Arg Phe Ser Gly
     50                  55                  60

Ser Gly Ser Gly Thr Asp Phe Asn Leu Thr Ile Ser Gly Leu Gln Pro
 65                  70                  75                  80

Asp Asp Phe Ala Thr Tyr Tyr Cys Leu Gln Tyr Asn Thr Tyr Ser Lys
                 85                  90                  95

Ser Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 39
<211> LENGTH: 214
<212> TYPE: PRT
<213> ORGANISM: Artificial Sequence
<220> FEATURE:
<223> OTHER INFORMATION: synthetically constructed MAB377 light chain
      amino acid

<400> SEQUENCE: 39

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ala Thr Ser
            20                  25                  30

Leu Ala Trp Tyr Gln Gln Lys Pro Gly Lys Ala Pro Arg Leu Leu Ile
        35                  40                  45

Tyr Ala Ala Ser Thr Leu Glu Ser Gly Val Pro Ser Arg Phe Ser Gly
50                  55                  60

Gly Gly Ser Gly Thr Asp Phe Thr Leu Thr Ile Ser Ser Leu Gln Pro
65                  70                  75                  80

Glu Asp Phe Ala Val Tyr Tyr Cys Gln Gln Val Asn Ser Tyr Pro Arg
                85                  90                  95

Thr Phe Gly Pro Gly Thr Lys Leu Asp Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 214
<212> TYPE: PRT
<213> ORGANISM: Artificial Sequence
<220> FEATURE:
<223> OTHER INFORMATION: synthetically constructed MAB378 light chain
      amino acid

<400> SEQUENCE: 40

```
Asp Ile Gln Met Thr Gln Ser Pro Ser Phe Leu Ser Ala Ser Val Gly
1               5                   10                  15

Asp Arg Val Thr Met Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Ile Tyr Tyr Cys Gln Gln Val Asn Gly Tyr Pro Arg
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 41
<211> LENGTH: 1599
<212> TYPE: DNA
<213> ORGANISM: Homo sapiens
<220> FEATURE:
<221> NAME/KEY: misc_feature
<222> LOCATION: (1)...(1599)
<223> OTHER INFORMATION: IgG1 light chain nucleotide sequence of
      constant region
<220> FEATURE:
<221> NAME/KEY: intron
<222> LOCATION: (289)...(685)
<220> FEATURE:
<221> NAME/KEY: intron
<222> LOCATION: (731)...(848)
<220> FEATURE:
<221> NAME/KEY: intron
<222> LOCATION: (1208)...(1277)

<400> SEQUENCE: 41
gcctccacca agggcccatc agtcttcccc ctggcaccct ctaccaagag cacctctggg      60
ggcacaacgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttggtgag     300
aggccagcac agggagggag ggtgtctgct ggaagccagg ctcagcgctc ctgcctggac     360
gcatcccggc tatgcagtcc cagtccaggg cagcaaggca ggccccgtct gcctcttcac     420
ccggaggcct ctgcccgccc cactcatgct caggagagg gtcttctggc ttttccccca     480
ggctctgggc aggcacaggc taggtgcccc taacccaggc cctgcacaca aaggggcagg     540
tgctgggctc agacctgcca agagccatat ccgggaggac cctgcccctg acctaagccc     600
accccaaagg ccaaactctc cactccctca gctcggacac cttctctcct cccagattcc     660
agtaactccc aatcttctct ctgcagagcc caaatcttgt gacaaaactc acacatgccc     720
```

```
accgtgccca ggtaagccag cccaggcctc gccctccagc tcaaggcggg acaggtgccc      780
tagagtagcc tgcatccagg acaggcccc agccgggtgc tgacacgtcc acctccatct       840
cttcctcagc acctgaactc ctgggggac cgtcagtctt cctcttcccc ccaaaaccca       900
aggacaccct catgatctcc cggacccctg aggtcacatg cgtggtggtg gacgtgagcc      960
acgaagaccc tgaggtcaag ttcaactggt acgtggacgg cgtggaggtg cataatgcca     1020
agacaaagcc gcgggaggag cagtacaaca gcacgtaccg tgtggtcagc gtcctcaccg     1080
tcctgcacca ggactggctg aatggcaagg agtacaagtg caaggtctcc aacaaagccc     1140
tcccagcccc catcgagaaa accatctcca aagccaaagg tgggacccgt ggggtgcgag     1200
ggccacatgg acagaggccg gctcggccca ccctctgccc tgagagtgac cgctgtacca     1260
acctctgtcc ctacagggca gccccgagaa ccacaggtgt acaccctgcc cccatcccgg     1320
gaggagatga ccaagaacca ggtcagcctg acctgcctgg tcaaaggctt ctatcccagc     1380
gacatcgccg tggagtggga gagcaatggg cagccggaga caactacaa gaccacgcct      1440 cccgtgctgg actccgacgg ctccttcttc ctctatagca agctcaccgt ggacaagagc     1500
aggtggcagc aggggaacgt cttctcatgc tccgtgatgc atgaggctct gcacaaccac     1560
tacacgcaga agagcctctc cctgtccccg ggtaaatga                            1599

<210> SEQ ID NO 42
<211> LENGTH: 363
<212> TYPE: DNA
<213> ORGANISM: Artificial Sequence
<220> FEATURE:
<223> OTHER INFORMATION: synthetically constructed MAB1 heavy chain
      variable domain nucleotide sequence

<400> SEQUENCE: 42
caggtgcagc tgcaggagtc gggcccagga ctggtgaagc cttcggagac cctgtccctc       60
atctgcagag tctctggtgg ctcgatcagt agtcattact ggagctggat ccggcagccc      120
ccagggaagg gactggagtg gattggatat atttcttata gggggagaag caaccacaat      180
ccttcccttg ggagacgagt ctctatgtca atagacacgt cggagaacca gttctccctg      240
aacctgagct ctgtgatcgc tgcggacacg gccgtatatt actgtgcgag agatgctact      300
gggatcagag aaatcaatgc tcttgatatc tggggccaag gacaacggt caccgtctct       360 tca                                                                    363

<210> SEQ ID NO 43
<211> LENGTH: 363
<212> TYPE: DNA
<213> ORGANISM: Artificial Sequence
<220> FEATURE:
<223> OTHER INFORMATION: synthetically constructed MAB8 heavy chain
      variable domain nucleotide sequence

<400> SEQUENCE: 43
gaggtgcagc tggtggagtc tgggggaggc ctggtcaagc ctgggggtc cctgagactc        60 tcctgtgcag cctctggttt cactttcagt acctatacta tgagttgggt ccgccaggct      120
ccagggcagg gctagagtg ggtctcgtcc attactagga ctagtagtaa tatatactac       180
gcagactcag tggagggccg attcaccatc tccagagaca cgccaagaa ctcactgtat       240 ctgcagatgc atagcctgag agtcgaagac acggctgtgt attactgtgc gagaatcagc      300
ggggtagtgg gacctgtccc ctttgactac tggggccagg gaaccctgat caccgtctcc      360
tct                                                                    363
```

<210> SEQ ID NO 44
<211> LENGTH: 354
<212> TYPE: DNA
<213> ORGANISM: Artificial Sequence
<220> FEATURE:
<223> OTHER INFORMATION: synthetically constructed MAB30 heavy chain
      variable domain nucleotide sequence

<400> SEQUENCE: 44

```
gaggtgcagc tggtggagtc tgggggaggc ttggtccagc ctggagggtc cctgagactc      60
tcctgtgcag cctctggatt caccttcagt gaccactaca tggactgggt ccgccaggct     120
ccagggaagg ggctggagtg ggttggccgt attagaaata agctgccat ttacaccaca      180 gaatacgccg cgtctgtgaa aggcagattc accatctcaa gagatgattt aaagagctca     240
gtgtatctgc aaatgaacag tctgaaaacc gacgacacgg ccatatatta ctgtgctagg     300
agctatggat actttgacta ctggggccag ggaaccctgg tcaccgtctc ctca           354
```

<210> SEQ ID NO 45
<211> LENGTH: 357
<212> TYPE: DNA
<213> ORGANISM: Artificial Sequence
<220> FEATURE:
<223> OTHER INFORMATION: synthetically constructed MAB42 heavy chain
      variable domain nucleotide sequence

<400> SEQUENCE: 45

```
caggtgcagc tggtacagtc tggggctgag gtgaagaagc ctggggcctc agtgaaggtc      60
tcctgcaagg cttctggata ttccttcaac ggctactata tgcactgggt gcgacaggcc     120
cctggacaag gcttgagtg gatgggttgg atcaacctga gcagtggtgg cacagattat      180
gcacagaaat tcaggggtg gtcactttg accagggaca cgtccatcac cacagcctac       240
atggagttga gcagcctgag atcgaacgac acggccgtgt attactgtgc gagaattaga     300
cctcgcactg gtgacttga ctcctggggc cagggaaccc tggtcatcgt ctcctca         357
```

<210> SEQ ID NO 46
<211> LENGTH: 363
<212> TYPE: DNA
<213> ORGANISM: Artificial Sequence
<220> FEATURE:
<223> OTHER INFORMATION: synthetically constructed MAB48 heavy chain
      variable domain nucleotide sequence

<400> SEQUENCE: 46

```
caggtgcagc tggtgcagtc tggggctgag gtgaagaagc ctgggtcctc ggtgaaagtc      60
tcctgcaagg cttctggagt caccttcacc gcctatgcta tcagttgggt gcgacaggcc     120
cctggacgag gcttgagtg gatgggaggg atcagcccctt tgtttggaat agtaaatttc     180
ggacagaact tccagggcag agtcacgatt accgcggaca aatccacggg cgcagcctac     240
atggagctga gcagcctgag ctctgaggac acggccatgt attactgtgc gagaggaccc     300
tattattacg atagaagtca cctagactac tggggccagg gaaccctggt caccgtctcc     360
tca                                                                   363
```

<210> SEQ ID NO 47
<211> LENGTH: 363
<212> TYPE: DNA
<213> ORGANISM: Artificial Sequence
<220> FEATURE:
<223> OTHER INFORMATION: synthetically constructed MAB49 heavy chain -continued variable domain nucleotide sequence

<400> SEQUENCE: 47

| caggtgcagc tggtgcagtc tggggctgag gtgaagaggc tgggtcctc ggtgaaggtc | 60 |
| tcctgcaagg cttctggagg caccttcagc agttatgcta ttagctgggt gcgacaggcc | 120 |
| cctggacaag ggcttgagtg gatgggaggg atcatcggta tgtttggaac aacaaactac | 180 |
| gcacagaagt tccagggcag agtcacgatt accgcggacg aattcacgag cacagcctac | 240 |
| atggagctga ccagcctgag atctgacgac acggccatgt attactgtgc gagagaccga | 300 |
| aattactatg cttcggggac ttatgaccac tggggccagg gaaccctggt caccgtctcc | 360 |
| tca | 363 |

<210> SEQ ID NO 48
<211> LENGTH: 360
<212> TYPE: DNA
<213> ORGANISM: Artificial Sequence
<220> FEATURE:
<223> OTHER INFORMATION: synthetically constructed MAB52 heavy chain
      variable domain nucleotide sequence

<400> SEQUENCE: 48

| caagtgctgc tggtgcagtc tggggctgaa gtgaagaagc ctgggtcctc ggtgaatatc | 60 |
| tcttgcaagg cttctggagg cactttcagc aactatgcta tctcctgggt gcgacaggcc | 120 |
| cctggacaag gtcttgactg gatgggaagg atcatcccta tctttggaac agcaaactac | 180 |
| gcacagaaat tccagggcag actcaccatt accgcggacg aatccacgag cacagcctac | 240 |
| atggaactga gcagcctgag atctgaagac acggccgtgt tttactgtgc gattactaaa | 300 |
| ccggggtctg tctacgcttt ggacgtctgg ggccaaggga ccacggtcac cgtctcctca | 360 |

<210> SEQ ID NO 49
<211> LENGTH: 360
<212> TYPE: DNA
<213> ORGANISM: Artificial Sequence
<220> FEATURE:
<223> OTHER INFORMATION: synthetically constructed MAB53 heavy chain
      variable domain nucleotide sequence

<400> SEQUENCE: 49

| caggtgcagc tggtgcagtc tggggctgag gtgaggaagc cggggtcctc ggtgaaggtc | 60 |
| tcctgcaagg tttctggagg catcattagg aaatatgcta tcaactgggt gcgacaggcc | 120 |
| cccggacaag ggcttgagtg gatgggaggg atcatcgcta tctttaatac agcaaactat | 180 |
| gcacagaaat tccagggcag agtcacgatt accgcggacg agtccacgag cacagtctac | 240 |
| atggagctga gcagcctgag atctgaagac acggcccttt attactgtgc gagaggaatg | 300 |
| aattactaca gtgactactt tgactactgg ggccagggaa gccttgtcac cgtctcccca | 360 |

<210> SEQ ID NO 50
<211> LENGTH: 360
<212> TYPE: DNA
<213> ORGANISM: Artificial Sequence
<220> FEATURE:
<223> OTHER INFORMATION: synthetically constructed MAB285 heavy chain
      variable domain nucleotide sequence

<400> SEQUENCE: 50

| caggtgcagc tggtgcagtc tggggctgag gtgaagaagc tggggcctc agtgaaggtc | 60 |
| tcctgccggg cttctggata caccttcacc ggctactata tgcagtgggt gcggcaggcc | 120 |

```
cctggccaag ggcttgagtg gatgggattc atcaatgcta acactggtgt cacaaacttt    180
gctcagaagt tcagggcag ggtcaccttg accagggaca cgtccatcag cacagcctac     240
atggagctga ggaggctgac atctgccgac acggccgtgt attactgtgc gagagcgccc    300
cagtggttat cgtattcttt tgatatctgg ggccaaggga caatggtcac cgtctcctca    360
```

<210> SEQ ID NO 51
<211> LENGTH: 369
<212> TYPE: DNA
<213> ORGANISM: Artificial Sequence
<220> FEATURE:
<223> OTHER INFORMATION: synthetically constructed MAB321 heavy chain
      variable domain nucleotide sequence

<400> SEQUENCE: 51

```
gaggtgcagc tggtggagtc tggggctgag gtgaggagcc ctggggcctc agtgaagctc     60
tcctgcaagg cttctgcata caccttcatc aactactatc tgcactgggt gcgacaggcc    120
cctggacaaa ggcttgagtg gatgggatgg atcaaccctg acagtggtgt cacagaatat    180
gcacagacat tcagggcag ggtcaccatg accagggaca cgtccatcaa tacagcctac     240
ctggacctgg agagactgac atctgacgac acggccgtat attactgtgc gagaggtttt    300
attccttggg gtgggaagta cttctacctt gactactggg gccagggaac cctggtcacc    360
gtctcctca                                                            369
```

<210> SEQ ID NO 52
<211> LENGTH: 381
<212> TYPE: DNA
<213> ORGANISM: Artificial Sequence
<220> FEATURE:
<223> OTHER INFORMATION: synthetically constructed MAB322 heavy chain
      variable domain nucleotide sequence

<400> SEQUENCE: 52

```
caggtacagc tgcagcagtc agggccagga ctggtgaagc cttcacagac cctgtccctc     60
acctgcagtg tatctggtag tttcatcaga agtggagatt ataattggag ttggatccgc    120
cagcccccag ggaagggcct ggagtggatt gggtacatcg ataatagcgg gagcacccac    180
tacaacccgt ccctcaagag tcgagttagc atatcagtgg acacgtccaa gaaccacttg    240
tccctgaagc tgagttttgt gactgacgca gacacgggcg tgtattactg tgccggagaa    300
caagcgtctg atagtcgtgg taattactac tactacgcta tggacgtctg gggccaaggg    360
accccggtca ccgtctcctc a                                              381
```

<210> SEQ ID NO 53
<211> LENGTH: 360
<212> TYPE: DNA
<213> ORGANISM: Artificial Sequence
<220> FEATURE:
<223> OTHER INFORMATION: synthetically constructed MAB375 heavy chain
      variable domain nucleotide sequence

<400> SEQUENCE: 53

```
caggtgcagc tgcagcagtc gggccccgga ctgatgaagc cttcggagac cctgtccctc     60
agctgcactg tctctggtga ctccgtcagt agttttttatt ggagttggat tcggcagtct    120
ccaggaaagg gactggagtg gattgggtat ttgctttaca gtgggaatac caagtataat    180
ccgtccctca agagtcgagc caccatatca gagacacgt ccaagaacca gttgtccctg     240
gagttgacct ctctgaccgc tgcggacacg gccgtctact attgtgcgag agtggtgaga    300
```
tggcgacatg gtggcgattt ggacgtctgg ggccaaggga ccacggtcac cgtctcctca    360

<210> SEQ ID NO 54
<211> LENGTH: 378
<212> TYPE: DNA
<213> ORGANISM: Artificial Sequence
<220> FEATURE:
<223> OTHER INFORMATION: synthetically constructed MAB376 heavy chain
      variable domain nucleotide sequence

<400> SEQUENCE: 54
caggtgcagc tggtgcagtc cggggggggac ttggtccagc cgggggggtc cctgagactg    60
tcatgtgcag tctctggatt catctttaga aaatatatca tgagttgggt ccggcaggct    120
ccagggaagg ggccggagtg ggtcgcagtt attagttcta gtggtgaccg gacattctac    180
gccgactccg tggagggccg cttcatcgtc tccagagaca attccaagga cacactgttt    240
ctgcaaatga acagcctgag aaccgaggac acggccatgt attactgtgc gaaagacctt    300
ttgggatttt gtagtggtgg tgattgcctg aaggtcttcg atctctgggg ccgaggcacc    360
atggtcactg tctcctca                                                 378

<210> SEQ ID NO 55
<211> LENGTH: 360
<212> TYPE: DNA
<213> ORGANISM: Artificial Sequence
<220> FEATURE:
<223> OTHER INFORMATION: synthetically constructed MAB377 heavy chain
      variable domain nucleotide sequence

<400> SEQUENCE: 55
caggtgcagc tgctgcagtc gggcccagga ctgataaagg cttcggagac cctgtctctc    60
agctgcagtg tctctaatga ctccgtcagt aattattatt ggagttggat ccggcagtcc    120
ccagagaagg gactggagtg gattgggtat ttgctttata gtgggaatac caagtacaat    180
ccctccctca agagtcgagc catcatatca agagacatgt ccaaaaatca gttgtccctc    240
agagtgactt ctgtgaccgc tgcggacacg gccatatatt attgtgcgcg agtggtgaga    300
tggcgatttg gtggtgatat ggacgtctgg ggtcaaggga ccgcggtcac cgtctccaca    360

<210> SEQ ID NO 56
<211> LENGTH: 360
<212> TYPE: DNA
<213> ORGANISM: Artificial Sequence
<220> FEATURE:
<223> OTHER INFORMATION: synthetically constructed MAB378 heavy chain
      variable domain nucleotide sequence

<400> SEQUENCE: 56
caggtgcagc tgcagcagtc gggcccagga ctgataaagc cttcggagac cctgtctctc    60
agctgctctg tctctggtga ctccgtcaat aattattatt ggagttggat ccggcagccc    120
ccagagaagg gactggagtg gattgggtat ctgcagtata gtgggagtac aaagtacaac    180
ccctccctca agagtcgagt caccatatca agagacacgt ccaaaaacca gttgtccctg    240
aagctgacct ctgtgaccgc tgcggacacg gccatatatt attgtgcgag agtggtgaga    300
tggcgacatg gtggggatat ggacgtctgg ggccaaggga ccgcggtcac cgtctcctct    360

<210> SEQ ID NO 57
<211> LENGTH: 324
<212> TYPE: DNA
<213> ORGANISM: Homo sapiens
<220> FEATURE:

<210> SEQ ID NO 57
<211> LENGTH: 324
<212> TYPE: DNA
<213> ORGANISM: Homo sapiens
<220> FEATURE:
<221> NAME/KEY: misc_feature
<222> LOCATION: (1)...(324)
<223> OTHER INFORMATION: light chain nucleotide sequence of constant
      kappa region

<400> SEQUENCE: 57
cgaactgtgg ctgcaccatc tgtcttcatc ttcccgccat ctgatgagca gttgaaatct        60
ggaactgcta gcgttgtgtg cctgctgaat aacttctatc ccagagaggc caaagtacag       120
tggaaggtgg ataacgccct ccaatcgggt aactcccagg agagtgtcac agagcaggac       180
agcaaggaca gcacctacag cctcagcagc accctgacgc tgagcaaagc agactacgag       240
aaacacaaag tctacgcctg cgaagtcacc catcagggcc tgagctcgcc cgtcacaaag       300
agcttcaaca ggggagagtg ttag                                              324

<210> SEQ ID NO 58
<211> LENGTH: 318
<212> TYPE: DNA
<213> ORGANISM: Homo sapiens
<220> FEATURE:
<221> NAME/KEY: misc_feature
<222> LOCATION: (1)...(318)
<223> OTHER INFORMATION: light chain nucleotide sequence of constant
      lambda region

<400> SEQUENCE: 58
ggtcagccca aggctgcccc ctctgtcact ctgttcccgc cctctagcga ggagcttcaa        60
gccaacaagg ccacactggt gtgtctcata agtgacttct acccgggagc cgtgacagtg       120
gcctggaagg cagatagcag ccccgtcaag gcgggagtgg agaccaccac accctccaaa       180
caaagcaaca acaagtacgc ggccagcagc tatctgagcc tgacgcctga gcagtggaag       240
tcccacagaa gctacagctg ccaggtcacg catgaaggga gcaccgtgga agacagtg         300 gtccctgcag aatgctct                                                     318

<210> SEQ ID NO 59
<211> LENGTH: 321
<212> TYPE: DNA
<213> ORGANISM: Artificial Sequence
<220> FEATURE:
<223> OTHER INFORMATION: synthetically constructed MAB1 light chain
      variable domain nucleotide sequence

<400> SEQUENCE: 59
gacatccaga tgacccagtc tccatcctcc ctgtctgcat ctggaggaga cagagtcacc        60
atcacttgcc gggcaagtca gagtgttagt acgtatttaa attggtatca gcagaaacca       120
gggaaagccc ctaacctcct ggtctatgct gtatccaatt tacaacgtgg cgtgccatca       180
aggttcagtg gcagtggatc tgggacacat ttcactctca caatcagcag tctgcaacct       240
gaggatttcg caacttacta ctgtcaacag agttacagtg accctctcac tttcggcgga       300
gggaccaagg tggagatcaa a                                                 321

<210> SEQ ID NO 60
<211> LENGTH: 324
<212> TYPE: DNA
<213> ORGANISM: Artificial Sequence
<220> FEATURE:
<223> OTHER INFORMATION: synthetically constructed MAB8 light chain
      variable domain nucleotide sequence

<400> SEQUENCE: 60
gacatccaga tgacccagtc tccatcttcc ctgtctgcat ctgtaggaga cagagtcacc        60

```
atcacttgcc gggcaagtca gaccattagc aagtatttaa attggtatca gcagaagcca    120
gggagagccc ctaaactcct gatctactct gcgtccagtt tgcaaagtgg ggtcccatca    180
aggttcactg gcagtggatc tgggacagat tcactctca ccatcaccag tctgcaacct     240
gaagattttg caacttacta ctgtcaacag agttacagac cctcccagat cactttcggc    300
cctgggacca aagtggatat caaa                                           324
```

<210> SEQ ID NO 61
<211> LENGTH: 321
<212> TYPE: DNA
<213> ORGANISM: Artificial Sequence
<220> FEATURE:
<223> OTHER INFORMATION: synthetically constructed MAB30 light chain
      variable domain nucleotide sequence

<400> SEQUENCE: 61

```
gacatccaga tgacccagtc tccttccacc ctgtctgcat ctgtaggaga cagagtcacc    60
atcacttgcc gggccagtca gagtattagt agttggttgg cctggtatca gcagaaacca   120
gggaacgccc ctaacctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatgatactt attctccgac gttcggccaa   300
gggaccaagg tggaaatcaa a                                             321
```

<210> SEQ ID NO 62
<211> LENGTH: 330
<212> TYPE: DNA
<213> ORGANISM: Artificial Sequence
<220> FEATURE:
<223> OTHER INFORMATION: synthetically constructed MAB42 light chain
      variable domain nucleotide sequence

<400> SEQUENCE: 62

```
cagtctgccc tgactcagcc tgcctccggg tctgggtctg ctggacaggc gatcaccatc    60
tcctgcactg gaaccggcac tgacgtctgt gcttataact tgtctcctg gtaccaacac    120 caccccggcg aagcccccaa actcatgatt tatgatgtca ataatcggcc ctcatgggtt   180
tctaatcgct tctctggctc caagtctggt aacacggcct ccctgaccat ctctgggctc   240
caggctgagg acgaggctga ttactactgc agctcatata aggaacgg cccttgcttg     300 ttcggcggag ggaccaagct gaccgtcctg                                    330
```

<210> SEQ ID NO 63
<211> LENGTH: 324
<212> TYPE: DNA
<213> ORGANISM: Artificial Sequence
<220> FEATURE:
<223> OTHER INFORMATION: synthetically constructed MAB48 light chain
      variable domain nucleotide sequence

<400> SEQUENCE: 63

```
gaaattgtgt tgacgcagtc tccaggcacc ctgtctttgt ctccagggga aagagccacc    60
ctctcctgca gggccagtca gagtgttggc agcagcgact tagcctggta ccagcagaaa   120
cctggccagg ctcccaggct cctcatatat ggtgcatcca gcgggccac tggcatccca    180 gacaggttca gtggcagtgg gtctgggaca gacttcactc tcaccatcag cagactggag   240
cctgaagatt ttgcagtgta ttactgtcag cagtatgtca gttcacccct cactttcggc   300
ggagggacca aggtggagat caag                                          324
```

<210> SEQ ID NO 64
<211> LENGTH: 321
<212> TYPE: DNA
<213> ORGANISM: Artificial Sequence
<220> FEATURE:
<223> OTHER INFORMATION: synthetically constructed MAB49 light chain
      variable domain nucleotide sequence

<400> SEQUENCE: 64
gacatccaga tgacccagtc tccatcctcc ctgtctgcat ctgtaggaga cagagtcacc    60
atcacttgcc gggcaagtca gagcattagc aggtatttaa attggtatca gcagaaacca   120
gggaaagccc ctaaactcct gatctattct gcatccagtt tgcaaagtgg ggtcccatca   180
aggttcggtg gcagtggatc tgggacagat ttcactctca ccatcagcag tctgcaacct   240
gaagattttg cactttacta ctgtcaacag acttacagta tcccgatcac cttcggccaa   300
gggacacgac tggactttaa a                                             321

<210> SEQ ID NO 65
<211> LENGTH: 324
<212> TYPE: DNA
<213> ORGANISM: Artificial Sequence
<220> FEATURE:
<223> OTHER INFORMATION: synthetically constructed MAB52 light chain
      variable domain nucleotide sequence

<400> SEQUENCE: 65
gacatccaga tgacccagtc tccatcctcc ctgtctgcat ctgtaggaga cagagtcact    60
atcacttgcc gggcaagtca gaccattagc acctatttaa attggtatca gcagaaacca   120
gggaaagccc ctaacctcct gatctatact gcatccagtt tgcaaagcgg ggtcccatca   180
agattcagtg gcagtggatc tgggacagat ttcactctca ccatcagcag tctgcaacct   240
gaagattttg caacttatta ctgtcaacag agttacgatg cccccacgtg gaccttcggc   300
ccagggacca aggtggaaat caaa                                          324

<210> SEQ ID NO 66
<211> LENGTH: 327
<212> TYPE: DNA
<213> ORGANISM: Artificial Sequence
<220> FEATURE:
<223> OTHER INFORMATION: synthetically constructed MAB53 light chain
      variable domain nucleotide sequence

<400> SEQUENCE: 66
gaaattgtgt tgacacagtc tccaggcacc ctgtctttgt ctccagggga aagagccacc    60
ctctcctgca gggccagtca gagtgttaga agcaacaact tagcctggta ccagcacaaa   120
cctggccagg ctcccaggct cctcatcttt ggtgcatcca gcagggccac tggcatccca   180
gacaggttca gtggcagtgg gtctgggaca gacttcactc tcaccatcag cagactggag   240
cctgaagatt ttgcagtata ttactgtcag cagtatggta gctcacctgc gctcactttc   300
ggcggaggga ccaaggtgga gatcaaa                                       327

<210> SEQ ID NO 67
<211> LENGTH: 330
<212> TYPE: DNA
<213> ORGANISM: Artificial Sequence
<220> FEATURE:
<223> OTHER INFORMATION: synthetically constructed MAB285 light chain
      variable domain nucleotide sequence

<400> SEQUENCE: 67

```
cagtctgtgc tgactcagcc accctcagcg tctgggaccc ccgggcagag ggtcaccatc    60
tcttgttctg gaagcagctc caacatcgga agtaatcctg taaactggta ccagcagctc   120
ccaggaacgg cccccagact tctcatctat agtaataatc agcggccctc aggggtccct   180
gaccgattct ctggctccaa gtctggcacc tcagcctccc tggccatcag tgggctccgg   240
tccgaggatg aggctgatta ctactgtaca tcatgggatg acagcctgaa tgcttgggtg   300
ttcggcgggg ggaccaggct gaccgtccta                                    330
```

<210> SEQ ID NO 68
<211> LENGTH: 321
<212> TYPE: DNA
<213> ORGANISM: Artificial Sequence
<220> FEATURE:
<223> OTHER INFORMATION: synthetically constructed MAB321 light chain
      variable domain nucleotide sequence

<400> SEQUENCE: 68

```
gatatcgtgt tgactcagtc tccaccctcc ctgtctgcat ctgtggggga cagagtcacc    60
atcacttgcc gggcaagtca gagcattaat aactacttaa attggtatca acagaaacca   120
gggaacgccc caagaatact aatctatggt gcatccagtt tggtaagtgg ggtcccatca   180
aggttcagtg gcagtggatc tgggacagat ttcaccctca ccatcagcag tctgcaacct   240
gaagattttg caacttacta ctgtcaacag agttaccggc ccctgtacac ttttggcccg   300
gggacccagc tggatgtcaa a                                             321
```

<210> SEQ ID NO 69
<211> LENGTH: 321
<212> TYPE: DNA
<213> ORGANISM: Artificial Sequence
<220> FEATURE:
<223> OTHER INFORMATION: synthetically constructed MAB322 light chain
      variable domain nucleotide sequence

<400> SEQUENCE: 69

```
gatatcgtga tgacccagtc tccatcttcc ctgtctgcat ctgtgggaga cagagtcacc    60
atcacttgcc gggcaagtga gagcattagc gcttatttaa attggtatca gcacacacca   120
gggagagccc ctaagctcct gatctatgct gcctccagtt tggaaactgg ggtcccatca   180
aggttcagtg gcagtggatc tggcacagaa ttcactctca ccatcagcgg tctgcaacct   240
gaagattttg tcacttacta ctgtcaacag acttacaata cccctcggac cttcggccaa   300
gggaccaagg tggaaatcaa a                                             321
```

<210> SEQ ID NO 70
<211> LENGTH: 321
<212> TYPE: DNA
<213> ORGANISM: Artificial Sequence
<220> FEATURE:
<223> OTHER INFORMATION: synthetically constructed MAB375 light chain
      variable domain nucleotide sequence

<400> SEQUENCE: 70

```
gatatccaga tgacccagtc tccatccttc ttgtctgcat ctgtgggaga cagagtcacc    60
ttcacttgcc gggccagtca gggcattgcc agttctttag cctggtatca gcaaaaagca   120
gggaaagccc ctaagctcct gatctatgct gcttctactt tggaagatgg ggtcccatca   180
aggttcagcg gcagtggatt tgggacagaa ttcactctca caatcaccag cctgcagcct   240
```

```
gaagattttg caacctatta ctgtcatcag gtgaatagtt accctcggac tttcggccct    300
gggaccacag tggatatcaa c                                              321
```

```
<210> SEQ ID NO 71
<211> LENGTH: 322
<212> TYPE: DNA
<213> ORGANISM: Artificial Sequence
<220> FEATURE:
<223> OTHER INFORMATION: synthetically constructed MAB376 light chain
      variable domain nucleotide sequence

<400> SEQUENCE: 71
gatatccaga tgacccagtc tccttccacc ctgtctgcat ctgtgggaga cacagtcacc    60
atcacttgcc gggccagtca gagtattagt acttggttgg cctggtttca gcagaaacca   120
gggagagccc ctaaactcct gatctatcag gcgtctagtt tggaaggtgg ggtcccatca   180
aggttcagcg gcagtgggtc tgggacagac ttcaacctca ccatcagcgg cctgcagcct   240
gatgattttg caacttatta ctgcctacaa tataacactt attcgaagtc attcggccaa   300
gggaccaagg tggaaatcaa ac                                            322
```

```
<210> SEQ ID NO 72
<211> LENGTH: 322
<212> TYPE: DNA
<213> ORGANISM: Artificial Sequence
<220> FEATURE:
<223> OTHER INFORMATION: synthetically constructed MAB377 light chain
      variable domain nucleotide sequence

<400> SEQUENCE: 72
gatatccaga tgacccagtc tccatccttc ttgtctgcat ctgtcggaga cagagtcacc    60
atcacctgcc gggccagtca gggcattgcc acttctttag cctggtatca gcaaaaacct   120
gggaaagccc cgaggctcct gatctatgct gcatccactt tggaaagtgg ggtcccatca   180
aggttcagcg gcggtggatc tgggacagac ttcactctca caatcagcag tctgcagccc   240
gaagattttg ctgtttatta ctgtcaacag gttaactcct atcctcggac tttcggccct   300
gggaccaaac tggatgtcaa ac                                            322
```

```
<210> SEQ ID NO 73
<211> LENGTH: 322
<212> TYPE: DNA
<213> ORGANISM: Artificial Sequence
<220> FEATURE:
<223> OTHER INFORMATION: synthetically constructed MAB378 light chain
      variable domain nucleotide sequence

<400> SEQUENCE: 73
gatatccaga tgacccagtc tccatccttc ttgtctgcat ctgtaggaga cagagtcacc    60
atgacctgcc gggccagtca gggcattagc agttatttag cctggtatca gcaaaaacca   120
gggaaagccc ctaagctcct gatctatgct gcatcgactt tggaaagtgg ggtcccatca   180
aggttcagcg gcagtggatc tgggacagaa ttcactctca caatcagcag cctgcagccc   240
gaagattttg caatttatta ctgtcaacag gttaatggtt accctcggac tttcggccct   300
gggaccaaag tggatatcaa ac                                            322
```

```
<210> SEQ ID NO 74
<211> LENGTH: 15
<212> TYPE: PRT
<213> ORGANISM: Artificial Sequence
<220> FEATURE:
```

<223> OTHER INFORMATION: synthetically constructed peptide derived from
      HA2

<400> SEQUENCE: 74

Arg Gly Leu Phe Gly Ala Ile Ala Gly Phe Ile Glu Asn Gly Trp
1               5                   10                  15

<210> SEQ ID NO 75
<211> LENGTH: 450
<212> TYPE: PRT
<213> ORGANISM: Artificial Sequence
<220> FEATURE:
<223> OTHER INFORMATION: synthetically constructed MAB53 heavy chain
      amino acid sequence

<400> SEQUENCE: 75

Gln Val Gln Leu Val Gln Ser Gly Ala Glu Val Arg Lys Pro Gly Ser
1               5                   10                  15

Ser Val Lys Val Ser Cys Lys Val Ser Gly Gly Ile Ile Arg Lys Tyr
            20                  25                  30

Ala Ile Asn Trp Val Arg Gln Ala Pro Gly Gln Gly Leu Glu Trp Met
        35                  40                  45

Gly Gly Ile Ile Ala Ile Phe Asn Thr Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Leu Tyr Tyr Cys
                85                  90                  95

Ala Arg Gly Met Asn Tyr Tyr Ser Asp Tyr Phe Asp Tyr Trp Gly Gln
            100                 105                 110

Gly Ser Leu Val Thr Val Ser Pro Ala Ser Thr Lys Gly Pro Ser Val
        115                 120                 125

Phe Pro Leu Val Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 76
<211> LENGTH: 216
<212> TYPE: PRT
<213> ORGANISM: Artificial Sequence
<220> FEATURE:
<223> OTHER INFORMATION: synthetically constructed MAB53 light chain
      amino acid sequence

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Asn Leu Ala Trp Tyr Gln His Lys Pro Gly Gln Ala Pro Arg Leu Leu
        35                  40                  45

Ile Phe Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

```
<210> SEQ ID NO 77
<211> LENGTH: 10
<212> TYPE: PRT
<213> ORGANISM: Artificial Sequence
<220> FEATURE:
<223> OTHER INFORMATION: synthetically constructed CDR1 region of
      IGHV1-69 01 heavy chain

<400> SEQUENCE: 77

Gly Gly Ile Ile Arg Lys Tyr Ala Ile Asn
1               5                   10

<210> SEQ ID NO 78
<211> LENGTH: 18
<212> TYPE: PRT
<213> ORGANISM: Artificial Sequence
<220> FEATURE:
<223> OTHER INFORMATION: synthetically constructed CDR2 region of
      IGHV1-69 01 heavy chain

<400> SEQUENCE: 78

Gly Gly Ile Ile Ala Ile Phe Asn Thr Ala Asn Tyr Ala Gln Lys Phe
1               5                   10                  15

Gln Gly

<210> SEQ ID NO 79
<211> LENGTH: 13
<212> TYPE: PRT
<213> ORGANISM: Artificial Sequence
<220> FEATURE:
<223> OTHER INFORMATION: synthetically constructed CDR3 region of
      IGHV1-69 01 heavy chain

<400> SEQUENCE: 79

Ala Arg Gly Met Asn Tyr Tyr Ser Asp Tyr Phe Asp Tyr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: synthetically constructed CDR1 region of
      IGKV3-20 01 light chain

<400> SEQUENCE: 80

Arg Ala Ser Gln Ser Val Arg Ser Asn Asn Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: synthetically constructed CDR2 region of
      IGKV3-20 01 light chain

<400> SEQUENCE: 81

Gly Ala Ser Ser Arg Ala Thr
1               5

<210> SEQ ID NO 82
<211> LENGTH: 10
<212> TYPE: PRT
<213> ORGANISM: Artificial Sequence
<220> FEATURE:
```

```
<223> OTHER INFORMATION: synthetically constructed CDR3 region of
      IGKV-20 01 light chain

<400> SEQUENCE: 82

Gln Gln Tyr Gly Ser Ser Pro Ala Leu Thr
1               5                   10

<210> SEQ ID NO 83
<211> LENGTH: 120
<212> TYPE: PRT
<213> ORGANISM: Artificial Sequence
<220> FEATURE:
<223> OTHER INFORMATION: synthetically constructed MAB53 heavy chain
      variable region IGHV1-69 01

<400> SEQUENCE: 83

Gln Val Gln Leu Val Gln Ser Gly Ala Glu Val Arg Lys Pro Gly Ser
1               5                   10                  15

Ser Val Lys Val Ser Cys Lys Val Ser Gly Gly Ile Ile Arg Lys Tyr
            20                  25                  30

Ala Ile Asn Trp Val Arg Gln Ala Pro Gly Gln Gly Leu Glu Trp Met
        35                  40                  45

Gly Gly Ile Ile Ala Ile Phe Asn Thr Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Leu Tyr Tyr Cys
                85                  90                  95

Ala Arg Gly Met Asn Tyr Tyr Ser Asp Tyr Phe Asp Tyr Trp Gly Gln
            100                 105                 110

Gly Ser Leu Val Thr Val Ser Pro
        115                 120

<210> SEQ ID NO 84
<211> LENGTH: 109
<212> TYPE: PRT
<213> ORGANISM: Artificial Sequence
<220> FEATURE:
<223> OTHER INFORMATION: synthetically constructed MAB53 light chain
      variable region IGKV3-20 01

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Asn Leu Ala Trp Tyr Gln His Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ala Leu Thr Phe Gly Gly Gly Thr Lys Val Glu Ile Lys
            100                 105
```

ANTIBODIES USEFUL IN PASSIVE INFLUENZA IMMUNIZATION

RELATED APPLICATIONS

This application claims priority to U.S. Provisional Patent Application Ser. No. 61/445,455 filed on 22 Feb. 2011, U.S. Provisional Patent Application Ser. No. 61/443,103 filed on 15 Feb. 2011, and U.S. Provisional Patent Application Ser. No. 61/355,978 filed on 17 Jun. 2010, the contents of which are incorporated in their entirety by reference herein.

REFERENCE TO SEQUENCE LISTING SUBMITTED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
|---|---|---|
| 388512012800seqlist.txt | Jun. 17, 2011 | 85,405 bytes |

TECHNICAL FIELD

The invention relates to the field of passive immunization against influenza. More particularly, antibodies that bind near to the $HA_0$ maturation cleavage site consensus sequence of influenza hemagglutinin A, including antibodies secreted by human cells.

BACKGROUND ART

The hemagglutinin protein of influenza virus has a globular head domain which is highly heterogeneous among flu strains and a stalk region containing a fusion site which is needed for entry into the cells. The hemagglutinin protein ($HA_0$) is activated to permit the fusion site to effect virulence by cleavage into $HA_1$ and $HA_2$ portions which remain coupled using disulfide bonds but undergo a conformational change. This cleavage site contains a consensus sequence which is shared both by influenza A and influenza B and by the various strains of influenza A and B.

Bianchi, E., et al., *J. Virol.* (2005) 79:7380-7388 describe a "universal" influenza B vaccine based on the consensus sequence of this cleavage site which was able to raise antibodies in mice when conjugated to the outer membrane protein complex of *Neisseria meningitidis*. Monoclonal antibodies which appear to bind to the consensus sequence were also described. In addition, successful passive transfer of antiserum was observed in mice. Prior vaccines, such as those described in WO2004/080403 comprising peptides derived from the M2 and/or HA proteins of influenza are subject to inducing antibodies that are either of weak efficacy or are not effective across strains.

DISCLOSURE OF THE INVENTION

The invention provides monoclonal antibodies that bind an epitope shared across multiple strains of influenza, and more particularly that bind representatives of either or both Group 1 and Group 2 influenza A. Such antibodies are able to confer passive immunity in the event of a pandemic caused, for example, by a previously unidentified influenza strain or a strain against which protection is not conferred by the seasonal vaccines currently available. Since the antibodies bind across many strains, indicative of targeting an essential site and thus likely to be included even in previously unencountered strain, such a vaccine would be effective in such circumstances. Such antibodies are also useful to ameliorate or prevent infection in subjects for whom vaccination failed to produce a fully protective response or who are at high risk due to a weak immune system (e.g., the very young, the elderly, transplant patients, cancer or HIV chemotherapy treated patients).

Thus, in one aspect, the invention is directed to monoclonal antibodies or immunoreactive fragments thereof that are broadly crossreactive with influenza A virus of Group 1 including H1, H2, H5, H6, H8, H9, H11, H13, H16 or Group 2 including H3 and H7 as type specimens, or that show cross-Group reactivity. The antibodies bind specifically to an epitope contained in the $HA_0$ protein of the influenza virus and recognize the native trimeric form of HA. As is well understood in the art, non-immunoglobulin based proteins may have similar epitope recognition properties as an antibody and can also provide suitable embodiments, including binding agents based on fibronectin, transferrin, lipocalin, or nucleic acid based aptamers.

In other aspects, the invention is directed to methods to use the antibodies and fragments of the invention for passively inhibiting viral infection in subjects. The invention is also directed to recombinant materials and methods to produce these antibodies or fragments.

BRIEF DESCRIPTION OF THE DRAWINGS

FIGS. 4A and 4B show the results of a FortéBio® assay demonstrating that MAB53 competes with MAB8, but not with MAB30.

FIGS. 5A and 5B show CDR mapping according to Kabat number of MAB53 heavy and light chain variable regions. IGHV1-69*01 is SEQ ID NO:83 and IGKV3-20*01 is SEQ ID NO:84.

FIG. 8 shows the effect of post-infection treatment of H5N1 with MAB53.

MODES OF CARRYING OUT THE INVENTION

Figure 1:
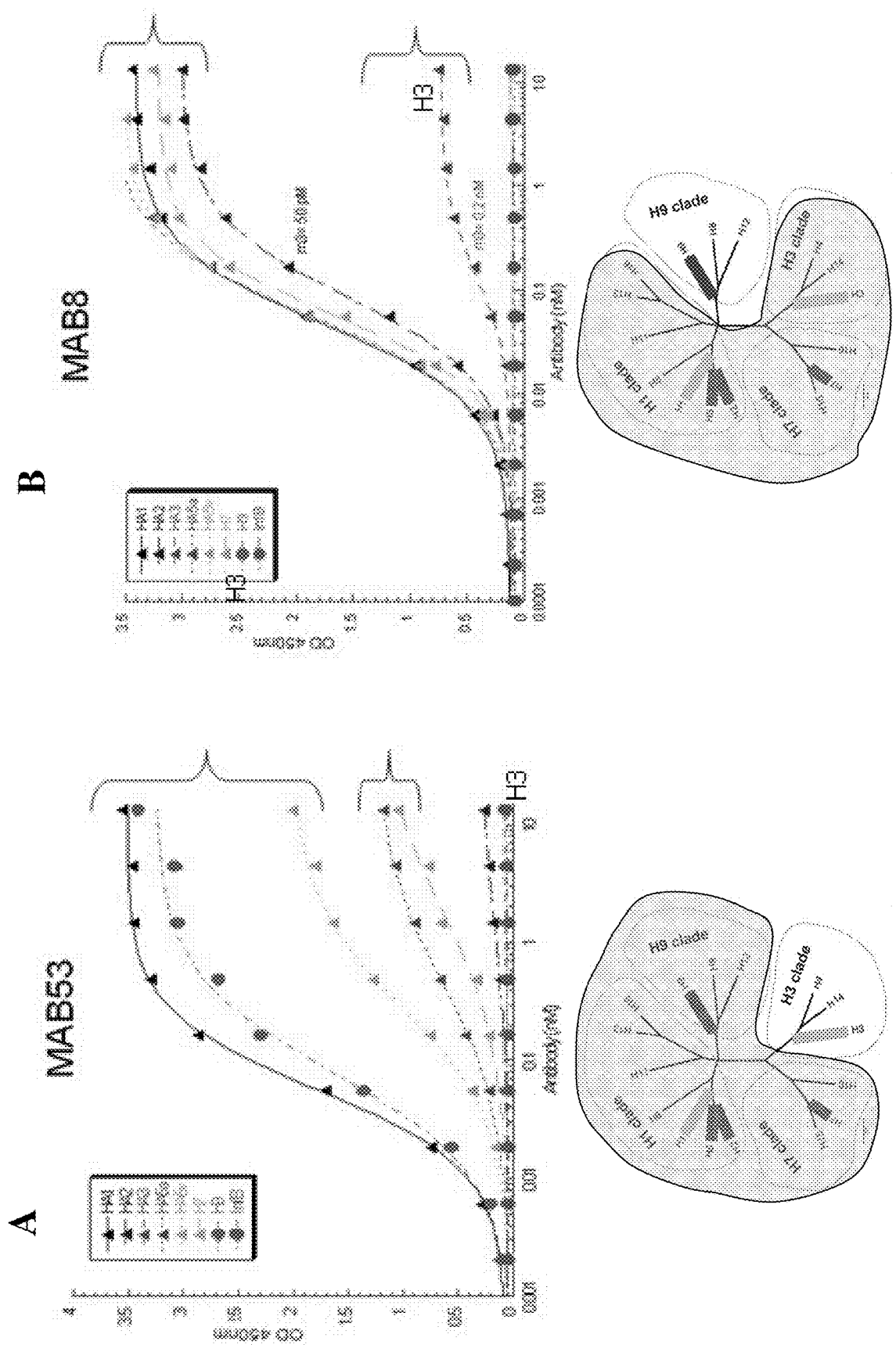
FIGS. 1A and 1B show the results of binding by MAB53 and MAB8 with respect to $HA_0$ protein from various influenza clades tested by ELISA.
FIG. 1C shows that MAB53 binds to native trimer, expressed in HEK293 cells.
Figure 1:
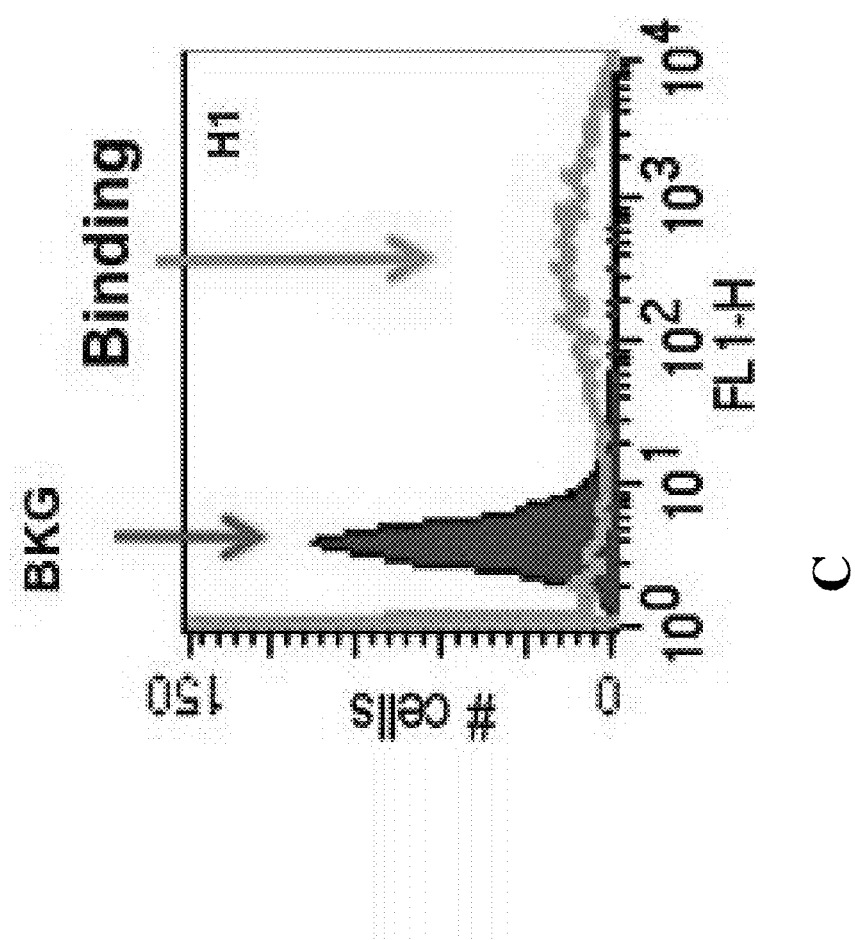
Figure 2:
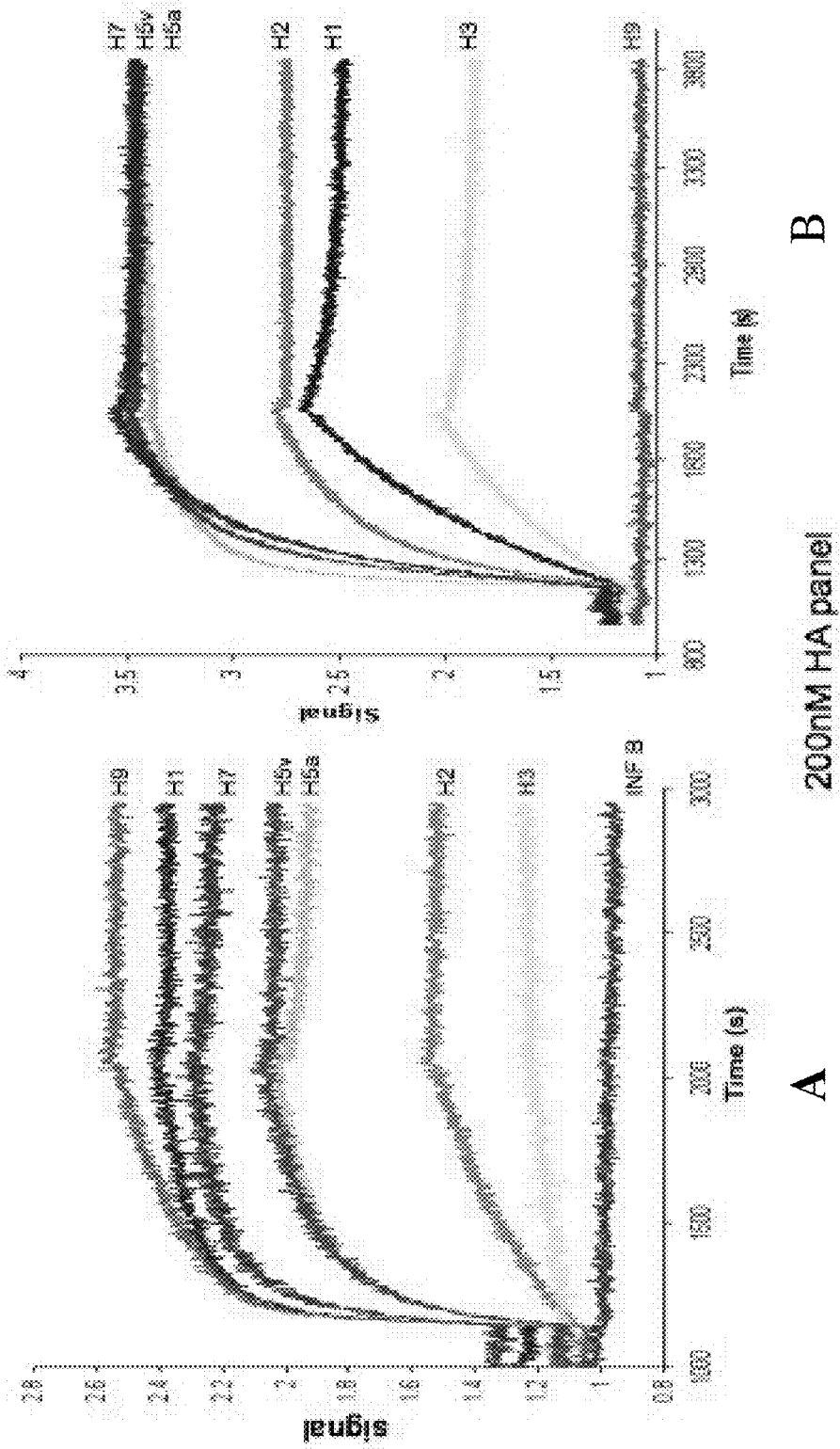
FIGS. 2A and 2B show the results of binding of MAB53 and MAB8 versus $HA_0$ protein from various clades as tested by FortéBio® biosensor.
Figure 3:
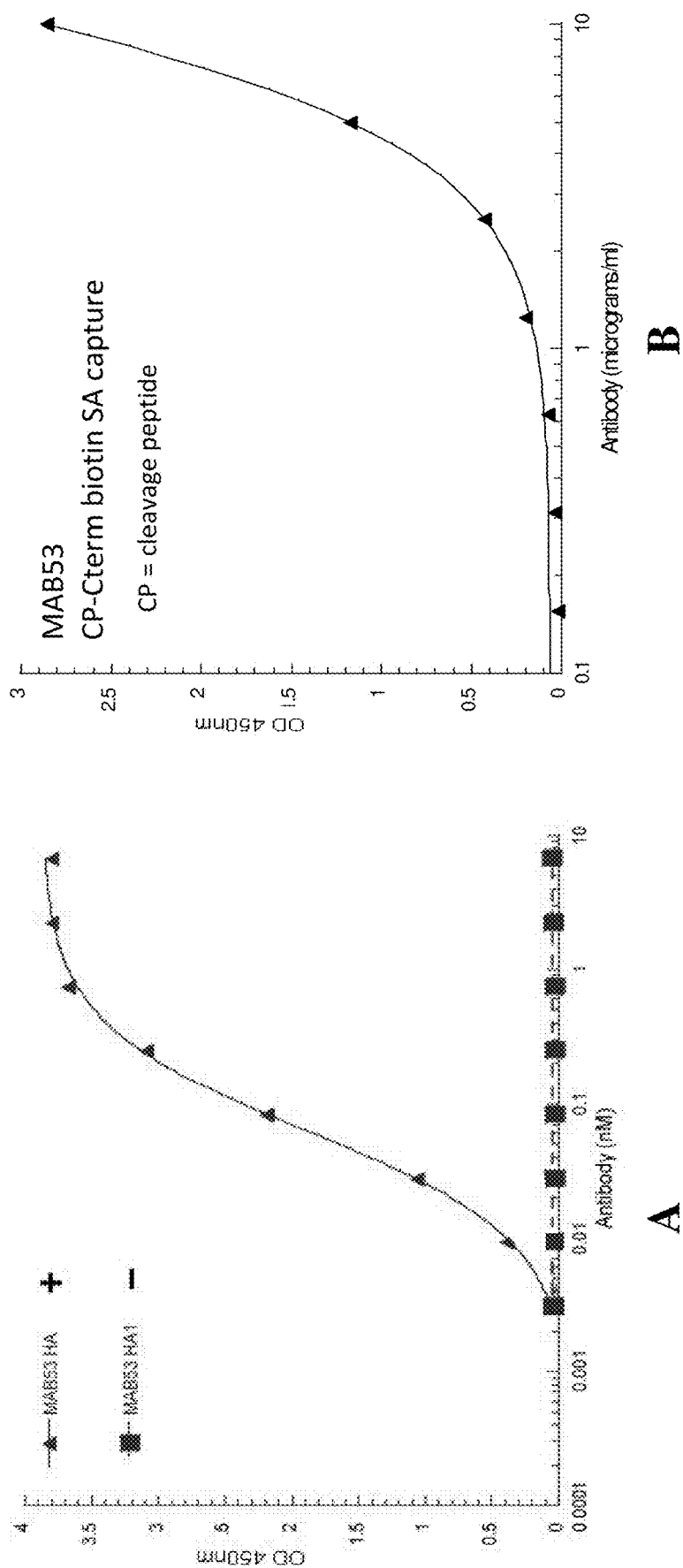
FIG. 3A shows the extent of binding as tested by ELISA of MAB53 with respect to $HA_0$ as an intact protein and the cleavage fragment $HA_1$.
FIG. 3B shows the extent of binding of MAB53 to a peptide denoted CP from $HA_2$.

The present invention provides useful antibodies including providing effective means to identify cells that secrete such antibodies so that the relevant coding sequences can be retrieved and stored for subsequent and facile recombinant production of such antibodies. The method includes a binary logic based design of a screening procedure.

Such a procedure can readily be applied to human cells using, in particular, the CellSpot™ method described in U.S. Pat. No. 7,413,868, the contents of which are incorporated herein by reference. Briefly, the method is able to screen individual cells obtained from human (or other) subjects in high throughput assays taking advantage of labeling with particulate labels and microscopic observation. In one illustrative embodiment, even a single cell can be analyzed for antibodies it secretes by allowing the secreted antibodies to be adsorbed on, or coupled to, a surface and then treating the surface with desired antigens each coupled to a distinctive particulate label. The footprint of a cell can therefore be identified with the aid of a microscope. Using this technique, millions of cells can be screened for desirable antibody secretions and even rare antibodies, such as those herein desirable for passive influenza immunization across strains can be recovered. Since human subjects have existing antibodies to at least some influenza strains, and since the antibodies obtained by the method of the invention bind a conserved sequence, these antibodies serve the purpose of addressing new strains as well as strains with which human populations have experience.

The invention provides a method to identify a monoclonal antibody that binds to a location near the hemagglutinin ($HA_0$) cleavage site consensus sequence. The method comprises contacting candidate monoclonal antibodies or fragments with: i) a peptide consisting essentially of an amino acid sequence upstream of or downstream of said consensus sequence, but lacking said consensus sequence; ii) a peptide consisting essentially of an amino acid sequence upstream of said consensus sequence and including said consensus sequence; and iii) a peptide consisting essentially of an amino acid sequence downstream of said consensus sequence and including said consensus sequence; wherein a monoclonal antibody that binds to the peptide of ii) and iii) but not to the peptide of i) is identified as a peptide that binds specifically to the $HA_0$ cleavage site consensus sequence. Other combinations could also be used, as will be evident to the skilled artisan, as long as binary logic is followed. For example, i) could be a peptide consisting essentially of an amino acid upstream of the consensus sequence of a first strain and lacking the consensus sequence, with ii) being the whole $HA_0$ sequence from the first strain and iii) being the whole $HA_0$ sequence from a second strain. Shorter portions could also be used. For further confirmation, an isolated peptide from the conserved region can also be used, although the information derived from the larger protein domains is believed to be more informative regarding recognition of the intact antigen.

This method is not limited to employing the CellSpot™ technique, nor is it limited to human antibodies. The binary logic of this method can be employed in any alternative screening method. Likewise, it can be applied to other diversity libraries besides natural immunoglobulins.

The method of the invention relies on binary logic wherein peptides that contain the desired consensus sequence and additional upstream and/or downstream portions are used as test peptides and their ability to complex antibodies as compared to regions lacking the consensus sequence is assessed. Thus, patterns are obtained whereby cells secreting the appropriate antibodies can be instantly identified.

In one illustrative embodiment, three antigens are used to assess the secreted antibody population. The first peptide is all or substantially all of the amino acid sequence upstream of the consensus sequence contained in $HA_0$ and is coupled to a particulate label of, say, red. A second test antigen contains these upstream sequences, but contains also the consensus sequence and is labeled with particle of a different color, for example, blue. A third test peptide contains the consensus sequence and all or substantially all of the downstream regions of the $HA_0$ protein and is labeled with a third color particulate, for example, green. (By upstream portion is meant toward the N-terminus from the consensus sequence and by downstream portion the continuation of the amino acid sequence from the consensus sequence toward the C-terminus. By "substantially all" is meant lacking only one or a few non-essential amino acids.) Antibodies that bind to the consensus sequence will bind both the green and blue particulate labeled peptides but will not bind the red labeled upstream sequence lacking the consensus sequence. If desired, the specificity can be confirmed by adding a fourth peptide representing only the downstream portion without the consensus sequence bound, for example, to a yellow particulate label, wherein the yellow particulate label will not be bound to the antibody. Of course, it does not matter whether the upstream or downstream portion is chosen as the negative control.

The cleavage site for various strains of influenza A and influenza B is known. For example, the above cited article by Bianchi, et al., shows in Table 1 the sequence around the cleavage site of several such strains:

TABLE 1

Consensus sequence of the solvent-exposed region of the influenza A and B virus maturational cleavage sites

| Virus/subtype | Strain | Sequence[a] | |
|---|---|---|---|
| A/H3/$HA_0$ | Consensus | NVPEKQTR (SEQ ID NO: 1) | ↓ GIFGAIAGFIE (SEQ ID NO: 2) |
| A/H1/$HA_0$ | Consensus | NIPSIQSR (SEQ ID NO: 3) | ↓ GLFGAIAGFIE (SEQ ID NO: 4) |
| B/$HA_0$ | Consensus[b] | PAKLLKER (SEQ ID NO: 5) | ↓ GFFGAIAGFLE (SEQ ID NO: 6) |

[a]The position of cleavage between $HA_1$ and $HA_2$ is indicated by the arrow.
[b]The consensus is the same for both the Victoria and Yamagata lineages.

As indicated, strict consensus occurs starting with the arginine residue upstream of the cleavage site and thus preferred consensus sequences included in the test peptides of the invention have the sequence RGI/L/F FGAIAGFLE (SEQ ID NO:7). It may be possible to use only a portion of this sequence in the test peptides.

Once cells that secrete the desired antibodies have been identified, it is straightforward to retrieve the nucleotide sequences encoding them and to produce the desired antibodies on a large scale recombinantly. This also enables manipulation of the antibodies so that they can be produced, for example, as single-chain antibodies or in terms of their variable regions only.

The retrieved nucleic acids may be physically stored and recovered for later recombinant production and/or the sequence information as to the coding sequence for the antibody may be retrieved and stored to permit subsequent synthesis of the appropriate nucleic acids. The availability of the information contained in the coding sequences and rapid synthesis and cloning techniques along with known methods of recombinant production permits rapid production of needed antibodies in the event of a pandemic or other emergency.

Applicants have recovered multiple monoclonal antibodies that are immunoreactive with $HA_0$ protein of influenza from multiple clades (SEQ ID NOS:9-23, 26-40, 42-56, and 59-73). Other sequences include the amino acid sequence for the human IgG1 heavy chain constant region (SEQ ID NO:8), the amino acid sequence for the human light chain constant kappa region (SEQ ID NO:24), the amino acid sequence for the human light chain constant lambda region (SEQ ID NO:25), the nucleotide sequence for the human heavy chain constant region (SEQ ID NO:41), the nucleotide sequence for the human light chain constant kappa region (SEQ ID NO:57), and the nucleotide sequence for the human light chain constant lambda region (SEQ ID NO:58).

Two of these mAbs, MAB53 and MAB8, have substantial crossreactivity among important, distantly related influenza clades. As shown in FIGS. 1A and B, each of these binds to three different clades with reasonable or high affinity. MAB53 binds to $HA_0$ from the H1, H9 and H7 clades and MAB8 binds to $HA_0$ protein from H1, H7 and H3 clades. The results shown in FIG. 1 were obtained by ELISA assay against $HA_0$ protein, and imply that the affinities are in the nanomolar range. Reactivity to native trimer of HA from all the Group 1 clades was verified using HA expressed in HEK293 cells with antibody binding measured by flow cytometry.

These results were confirmed using an alternative assay system, the biolevel interferometry based binding assay designated FortéBio® biosensor, as shown in FIGS. 2A and 2B. As measured by this more accurate assay, the affinities are as follows:

MAB53/H1=60 pM, H5=6 nM, H7=70 pM, H9=30 pM;
MAB8/H1=9 nM, H3=16 nM, H5=0.2 nM.

Both MAB53 and MAB8 are fully human antibodies, but similar antibodies characteristic of other species are also included in the invention. In the context of the invention, "antibodies" and their fragments include those portions of the molecule that are relevant for binding; thus, fragments would include variable regions only and "antibodies" as a general term would also be considered to include such fragments. Thus, $F_{ab}$ fragments, $F_{(ab')_2}$, and Fv fragments are included as well as recombinantly produced single chain antibodies, and fusions of such constructs to create bispecific agents. Chimeric, humanized and human antibodies are all within the scope of the present invention as are antibody mimics based on other protein scaffolds such as fibronectin, transferrin, or lipocalin. Likewise, multiple technologies now exist for making a single antibody-like molecule that incorporates antigen specificity domains from two separate antibodies (bi-specific antibody). Thus, a single antibody with very broad strain reactivity can be constructed using the Fab domains of individual antibodies with broad reactivity to Group 1 and Group 2 respectively. Suitable technologies have been described by Macrogenics (Rockville, Md.), Micromet (Bethesda, Md.) and Merrimac (Cambridge, Mass.). (See, e.g., Orcutt K D, Ackerman M E, Cieslewicz M, Quiroz E, Slusarczyk A L, Frangioni J V, Wittrup K D. A modular IgG-scFv bispecific antibody topology, *Protein Eng Des Sel*. (2010) 23:221-228; Fitzgerald J, Lugovskoy A. Rational engineering of antibody therapeutics targeting multiple oncogene pathways. *MAbs*. (2011) 1:3(3); Baeuerle P A, Reinhardt C. Bispecific T-cell engaging antibodies for cancer therapy. *Cancer Res*. (2009) 69:4941-4944.)

To identify the epitope to which MAB53 binds, ELISA assays were conducted with respect to uncleaved $HA_0$ protein, the $HA_1$ fragment, and the $HA_2$ fragment. As shown in FIGS. 3A and B, while MAB53 binds with high affinity to $HA_0$, it does not bind $HA_1$ implying binding to the complementary HA2 fragment. To confirm this hypothesis, a peptide derived from $HA_2$ was immobilized on a streptavidin coated plate using a C-terminal biotin. Specifically, the sequence tested was RGLFGAIAGFIENGW (SEQ ID NO:74). Irrelevant flanking portions were also used. MAB53 was confirmed as capable of binding to this peptide. As MAB53 does not bind to $HA_0$ when tested by Western blot, it is assumed that the dominant epitope is at least in part conformational in nature.

It has also been found that MAB8 and MAB53 bind to the same or nearby epitopes as demonstrated by their ability to compete with each other for binding to the $HA_0$ protein of the H1 clade. This was shown using a FortéBio® assay using 2 μg/ml of antibody and 50 nM $HA_0$ from H1. As shown in FIG. 4A, the signal obtained from MAB53 bound to the FortéBio® surface is augmented when 50 nM $HA_0$ solution is added. However, when MAB8 is then added, no further signal occurs. Thus, MAB53 blocks the epitope bound by MAB8. As shown in FIG. 4B, however, another antibody that is immunoreactive with $HA_0$, MAB30, binds, apparently, to a different epitope as the signal is enhanced when it is added to the coupled MAB53-$HA_0$.

Importantly, MAB53 and MAB8 differ in that MAB8 is released from the $HA_0$ protein when the pH is lowered to 6, whereas MAB53 is not. This difference is significant as this appears predictive of neutralizing capability. In tests for the ability of MAB8 to neutralize H1N1 viral infection in a plaque reduction assay in MDCK target cells, low doses of MAB53 of 1-5 μg/ml neutralized infection by H1N1, by H7N3, H5N1 and H9N2. However, MAB8 does not neutralize infection by these strains. Thus, neutralizing strains may be preferentially selected by washing bound MAB or fragment at pH 6 during the primary screen, thus removing from $HA_0$ MAB's that are unlikely to remain bound as the antibody-virus complex enters the cell via the endosomal compartment and thus will be expected to have reduced ability to neutralize the virus.

For example, in the CellSpot method $HA_0$ may be bound to solid support (fluorescent beads) and captured by the MAB or a mixture of MAB's, then washed at pH 6.

MAB53 is produced recombinantly and has been sequenced. The full-length sequences of the heavy chain and light chain are as follows:

Heavy Chain:
(SEQ ID NO: 75)
QVQLVQSGAEVRKPGSSVKVSCKVSGGIIRKYAINWVRQAPGQGLEWMGG
IIAIFNTANYAQKFQGRVTITADESTSTVYMELSSLRSEDTALYYCARGM
NYYSDYFDYWGQGSLVTVSPASTKGPSVFPLVPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG
K;
and Light Chain:
(SEQ ID NO: 76)
EIVLTQSPGTLSLSPGERATLSCRASQSVRSNNLAWYQHKPGQAPRLLIF
GASSRATGIPDRFSGSGSGTDFTLTISRLEPEDFAVYYCQQYGSSPALTF

-continued

```
GGGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC.
```

The bold sequences are variable domains, and the unbolded sequences represent the IgG1 constant chain for the heavy chain and the kappa constant chain for the light chain.

In addition, these variable regions have been analyzed according to the Kabat CDR assessment based on matching framework regions. As shown in FIG. 5A, CDR1, CDR2, and CDR3 of the IGHV1-69*01 heavy chain (SEQ ID NO:83) are GGIIRKYAIN (SEQ ID NO:77), GGIIAIFN-TANYAQKFQG (SEQ ID NO:78) and ARGMNYYS-DYFDY (SEQ ID NO:79), respectively. As shown in FIG. 5B, CDR1, CDR2, and CDR3 of the IGKV3-20*01 light chain (SEQ ID NO:84) are RASQSVRSNNLA (SEQ ID NO:80), GASSRAT (SEQ ID NO:81) and QQYGSSPALT (SEQ ID NO:82), respectively.

Figure 6:
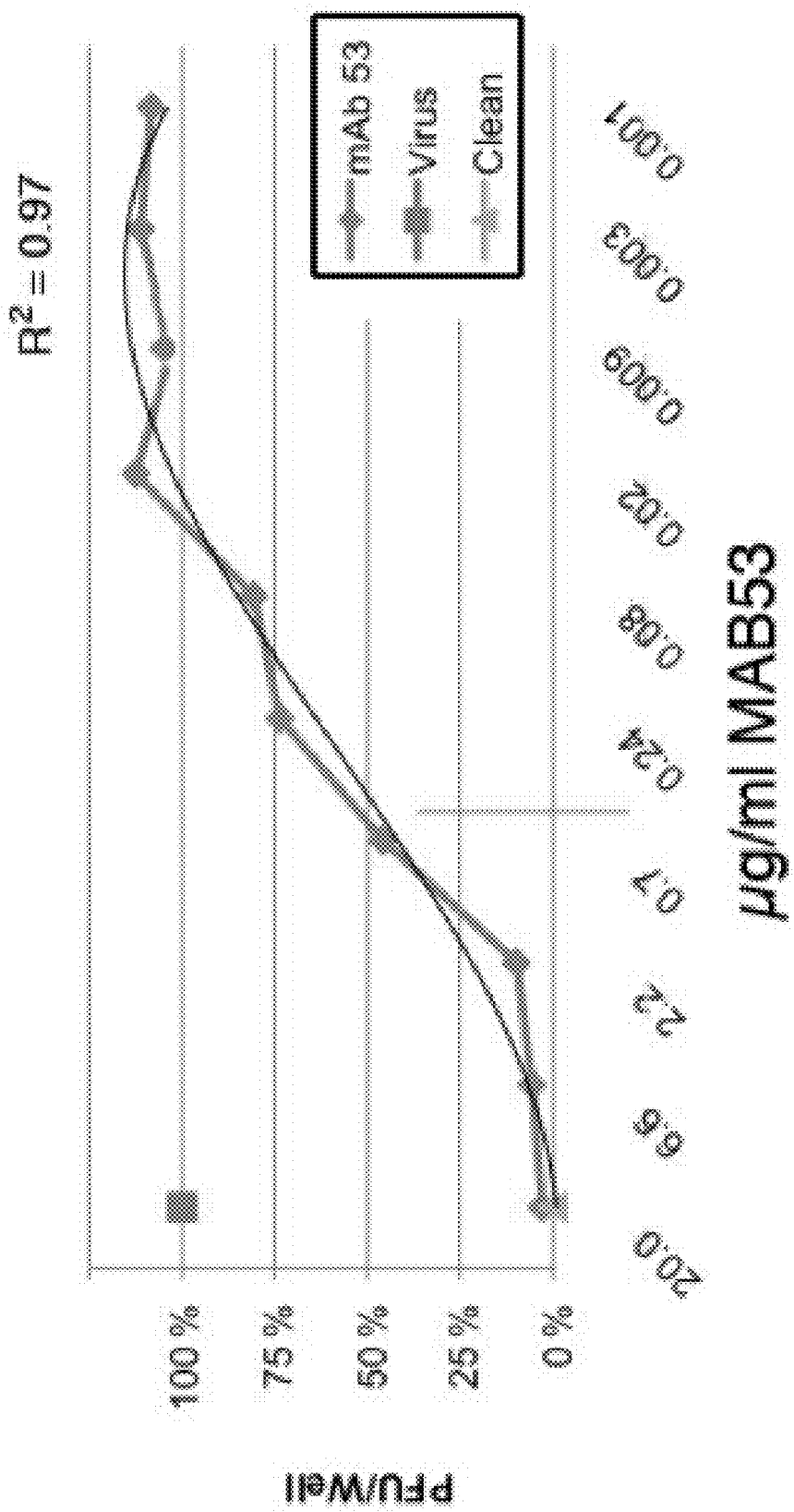
FIG. 6 shows neutralization of H1N1 by various amounts of MAB53, as measured by in vitro plaque assay.

As shown in FIG. 6, MAB53 neutralizes H1N1 in vitro in a plaque assay.

Figure 7:
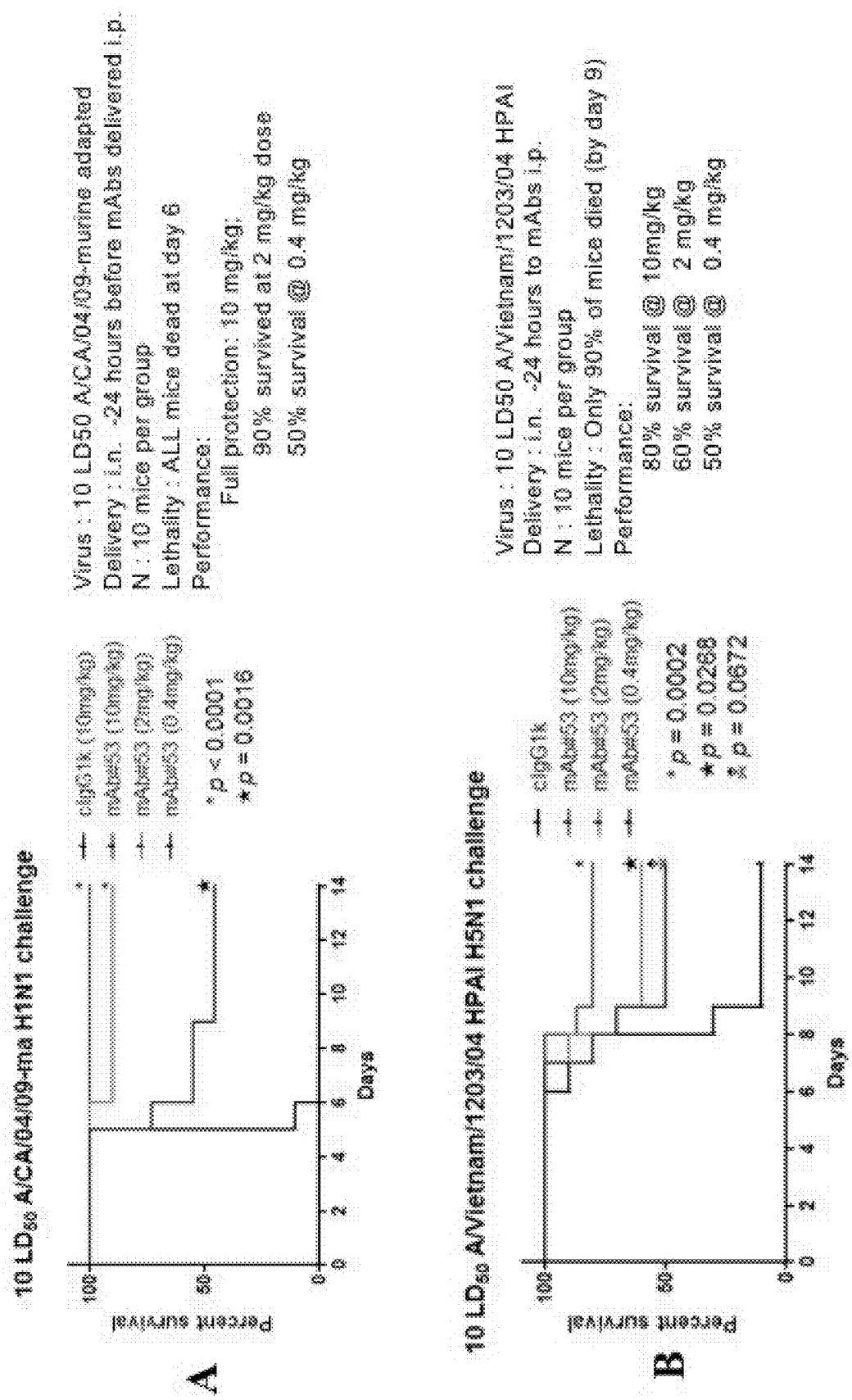
FIGS. 7A and 7B show survival times for mice challenged with H1N1 (panel A) or H5N1 (panel B) as a function of administration of various amounts of MAB53.

It has also been shown that mice pretreated with graded doses of MAB53 survive challenge with otherwise lethal titers of H1N1 and H5N1 viruses with 100% protection against H1N1 challenge, as shown in FIG. 7. The potency is comparable to a prior art antibody described by Crucell which does not show activity against Group 2 strains. Throsby M., et al., *PLoS One*. (2008) 3:e3942. Epub 2008 Dec. 16. These are heterosubtypic neutralizing monoclonal antibodies cross-protective against H5N1 and H1N1 recovered from human IgM+ memory B cells.

As shown in FIG. 7A, MAB53 provided full protection at 10 mg/kg; 90% survived at 2 mg/kg and 50% survived at 0.4 mg/kg. In comparison, the prior art antibody from Crucell gave full protection at 2 mg/kg, but only 20% survived when 0.7 mg/kg were administered. This is despite the fact that the lethality of the viral dose was less than that in the experiment shown in FIG. 7A; only 90% of the mice died after infection, whereas in the experiment shown in FIG. 7A, all the mice died at day 6. This demonstrates that MAB53 is highly potent.

Where challenge by H5N1 was substituted for challenge by H1N1, for MAB53 shown in FIG. 7B, 10 mg/kg gave 80% survival; 2 mg/kg gave 60% survival and 0.4 mg/kg gave 50% survival. In comparison, for the prior art antibody, 100% survival was obtained at 5 mg/kg and 60% survival at 1.7 mg/kg. Thus, the survival rates at 1.7 mg/kg and 2 mg/kg were comparable. In this case, the viral dose itself was slightly less potent in the mice tested with MAB53.

Figure 8:
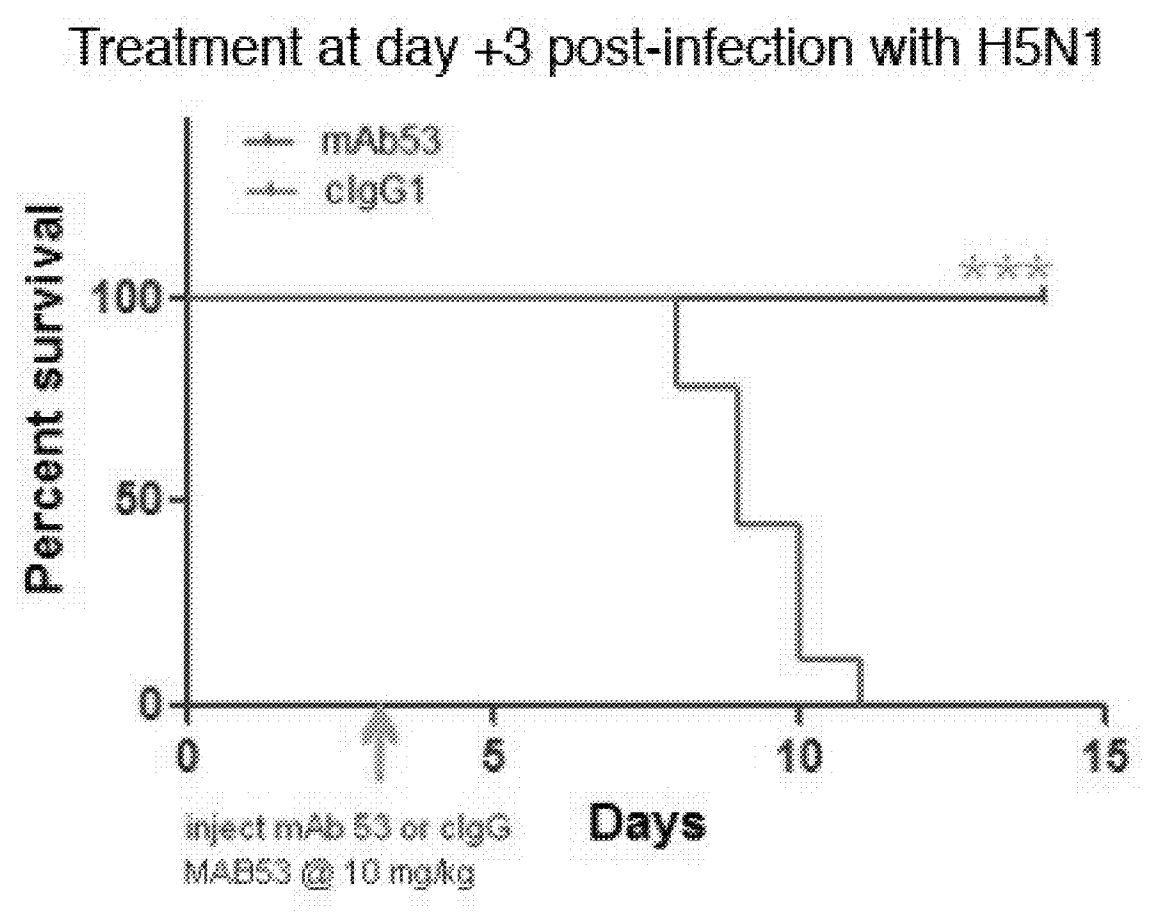

As shown in FIG. 8, MAB53 (10 mg/kg) was administered as a post-infection treatment at day +3 against the high pathology H5N1 strain. The control antibody is isotype matched but does not recognize any flue antigen. The infection and treatment protocol is the same as that for FIG. 7A, but given at day +3 instead of day −1.

Pepscan analysis was performed, establishing that MAB53 and CR6261 bind to similar regions of HA, but different epitopes (data not shown). This is consistent with the different activity of the two antibodies.

Thus, MAB53 and antibodies that bind to the same epitope under the same conditions are effective as passive vaccines suitable for protection of populations against epidemics and pandemics, and for prophylactic or therapeutic use against seasonal influenza for patients with a weakened immune system.

```
                       SEQUENCE LISTING

NVPEKQTR (SEQ ID NO: 1)

GIFGAIAGFIE (SEQ ID NO: 2)

NIPSIQSR (SEQ ID NO: 3)

GLFGAIAGFIE (SEQ ID NO: 4)

PAKLLKER (SEQ ID NO: 5)

GFFGAIAGFLE (SEQ ID NO: 6)

RGI/L/FFGAIAGFLE (SEQ ID NO: 7).

Human IgG1 HC amino acid sequence of constant region (SEQ ID NO: 8)
ASTKGPSVFPLVPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK MAB1 HC amino acid sequence of variable domain (SEQ ID NO: 9)
QVQLQESGPGLVKPSETLSLICRVSGGSISSHYWSWIRQPPGKGLEWIGYISYRGRS
NHNPSLGRRVSMSIDTSENQFSLNLSSVIAADTAVYYCARDATGIREINALDIWGQG
TTVTVSS MAB8 HC amino acid sequence of variable domain (SEQ ID NO: 10)
EVQLVESGGGLVKPGGSLRLSCAASGFTFSTYTMSWVRQAPGQGLEWVSSITRTSSN
IYYADSVEGRFTISRDNAKNSLYLQMHSLRVEDTAVYYCARISGVVGPVPFDYWGQG
TLITVSS MAB30 HC amino acid sequence of variable domain (SEQ ID NO: 11)
EVQLVESGGGLVQPGGSLRLSCAASGFTFSDHYMDWVRQAPGKGLEWVGRIRNKAAI
YTTEYAASVKGRFTISRDDLKSSVYLQMNSLKTDDTAIYYCARSYGYFDYWGQGTLV
TVSS
```

```
MAB42 HC amino acid sequence of variable domain (SEQ ID NO: 12)
QVQLVQSGAEVKKPGASVKVSCKASGYSFNGYYMHWVRQAPGQGLEWMGWINLSSGG
TDYAQKFQGWVTLTRDTSITTAYMELSSLRSNDTAVYYCARIRPRTGGLDSWGQGTL
VIVSS MAB48 HC amino acid sequence of variable domain (SEQ ID NO: 13)
QVQLVQSGAEVKKPGSSVKVSCKASGVTFTAYAISWVRQAPGRGLEWMGGISPLFGI
VNFGQNFQGRVTITADKSTGAAYMELSSLSSEDTAMYYCARGPYYYDRSHLDYWGQG
TLVTVSS MAB49 HC amino acid sequence of variable domain (SEQ ID NO: 14)
QVQLVQSGAEVKRPGSSVKVSCKASGGTFSSYAISWVRQAPGQGLEWMGGIIGMFGT
TNYAQKFQGRVTITADEFTSTAYMELTSLRSDDTAMYYCARDRNYYASGTYDHWGQG
TLVTVSS MAB52 HC amino acid sequence of variable domain (SEQ ID NO: 15)
QVLLVQSGAEVKKPGSSVNISCKASGGTFSNYAISWVRQAPGQGLDWMGRIIPIFGT
ANYAQKFQGRLTITADESTSTAYMELSSLRSEDTAVFYCAITKPGSVYALDVWGQGT
TVTVSS MAB53 HC amino acid sequence of variable domain (SEQ ID NO: 16)
QVQLVQSGAEVRKPGSSVKVSCKVSGGIIRKYAINWVRQAPGQGLEWMGGIIAIFNT
ANYAQKFQGRVTITADESTSTVYMELSSLRSEDTALYYCARGMNYYSDYFDYWGQGS
LVTVSP MAB285 HC amino acid sequence of variable domain (SEQ ID NO: 17)
QVQLVQSGAEVKKPGASVKVSCRASGYTFTGYYMQWVRQAPGQGLEWMGFINANTGV
TNFAQKFQGRVTLTRDTSISTAYMELRRLTSADTAVYYCARAPQWLSYSFDIWGQGT
MVTVSS MAB321 HC amino acid sequence of variable domain (SEQ ID NO: 18)
EVQLVESGAEVRSPGASVKLSCKASAYTFINYYLHWVRQAPGQRLEWMGWINPDSGV
TEYAQTFQGRVTMTRDTSINTAYLDLERLTSDDTAVYYCARGFIPWGGKYFYLDYWG
QGTLVTVSS MAB322 HC amino acid sequence of variable domain (SEQ ID NO: 19)
QVQLQQSGPGLVKPSQTLSLTCSVSGSFIRSGDYNWSWIRQPPGKGLEWIGYIDNSG
STHYNPSLKSRVSISVDTSKNHLSLKLSFVTDADTGVYYCAGEQASDSRGNYYYYAM
DVWGQGTPVTVSS MAB375 HC amino acid sequence of variable domain (SEQ ID NO: 20)
QVQLQQSGPGLMKPSETLSLSCTVSGDSVSSFYWSWIRQSPGKGLEWIGYLLYSGNT
KYNPSLKSRATISRDTSKNQLSLELTSLTAADTAVYYCARVVRWRHGGDLDVWGQGT
MVTVSS MAB376 HC amino acid sequence of variable domain (SEQ ID NO: 21)
QVQLVQSGGDLVQPGGSLRLSCAVSGFIFRKYIMSWVRQAPGKGPEWVAVISSSGDR
TFYADSVEGRFIVSRDNSKDTLFLQMNSLRTEDTAMYYCAKDLLGFCSGGDCLKVFD
LWGRGTMVTVSS MAB377 HC amino acid sequence of variable domain (SEQ ID NO: 22)
QVQLLQSGPGLIKASETLSLSCSVSNDSVSNYYWSWIRQSPEKGLEWIGYLLYSGNT
KYNPSLKSRAIISRDMSKNQLSLRVTSVTAADTAIYYCARVVRWRFGGDMDVWGQGT
AVTVST MAB378 HC amino acid sequence of variable domain (SEQ ID NO: 23)
QVQLQQSGPGLIKPSETLSLSCSVSGDSVNNYYWSWIRQPPEKGLEWIGYLQYSGST
KYNPSLKSRVTISRDTSKNQLSLKLTSVTAADTAIYYCARVVRWRHGGDMDVWGQGT
AVTVSS Human LC amino acid sequence of constant kappa region (SEQ ID NO: 24)
RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC Human LC amino acid sequence of constant lambda region (SEQ ID NO: 25)
GQPKAAPSVTLFPPSSEELQANKATLVCLISDFYPGAVTVAWKADSSPVKAGVETTT
PSKQSNNKYAASSYLSLTPEQWKSHRSYSCQVTHEGSTVEKTVVPAECS MAB1 LC amino acid sequence (SEQ ID NO: 26)
DIQMTQSPSSLSASGGDRVTITCRASQSVSTYLNWYQQKPGKAPNLLVYAVSNLQRG
VPSRFSGSGSGTHFTLTISSLQPEDFATYYCQQSYSDPLTFGGGTKVEIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC
```

SEQUENCE LISTING

MAB8 LC amino acid sequence (SEQ ID NO: 27)
DIQMTQSPSSLSASVGDRVTITCRASQTISKYLNWYQQKPGRAPKLLIYSASSLQSG
VPSRFTGSGSGTDFTLTITSLQPEDFATYYCQQSYRPSQITFGPGTKVDIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC MAB30 LC amino acid sequence (SEQ ID NO: 28)
DIQMTQSPSTLSASVGDRVTITCRASQSISSWLAWYQQKPGNAPNLLIYKASSLESG
VPSRFSGSGSGTEFTLTISSLQPDDFATYYCQQYDTYSPTFGQGTKVEIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC MAB42 LC amino acid sequence (SEQ ID NO: 29)
QSALTQPASVSGSAGQSITISCTGTSSDVGAYNFVSWYQHHPGKAPKLMIYDVDNRP
SGVSNRFSGSKSGDTASLTISGLQAEDEADYYCSSYRRNGPWVFGGGTKLTVLGQPK
AAPTVTLFPPSSEELQANKATLVCLISDFYPGAVTVAWKADSSPVKAGVETTTPSKQ
SNNKYAASSYLSLTPEQWKSHRSYSCQVTHEGSTVEKTVVPAECS MAB48 LC amino acid sequence (SEQ ID NO: 30)
EIVLTQSPGTLSLSPGERATLSCRASQSVGSSDLAWYQQKPGQAPRLLIYGASSRAT
GIPDRFSGSGSGTDFTLTISRLEPEDFAVYYCQQYVSSPLTFGGGTKVEIKR
TVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC MAB49 LC amino acid sequence (SEQ ID NO: 31)
DIQMTQSPSSLSASVGDRVTITCRASQSISRYLNWYQQKPGKAPKLLIYSASSLQSG
VPSRFGGSGSGTDFTLTISSLQPEDFALYYCQQTYSIPITFGQGTRLDFKR
**TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC**

MAB52 LC amino acid sequence (SEQ ID NO: 32)
DIQMTQSPSSLSASVGDRVTITCRASQTISTYLNWYQQKPGKAPNLLIYTASSLQSG
VPSRFSGSGSGTDFTLTISSLQPEDFATYYCQQSYDAPTWTFGPGTKVEIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC MAB53 LC amino acid sequence (SEQ ID NO: 33)
EIVLTQSPGTLSLSPGERATLSCRASQSVRSNNLAWYQHKPGQAPRLLIFGASSRAT
GIPDRFSGSGSGTDFTLTISRLEPEDFAVYYCQQYGSSPALTFGGGTKVEIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC MAB285 LC amino acid sequence (SEQ ID NO: 34)
QSVLTQPPSASGTPGQRVTISCSGSSSNIGSNPVNWYQQLPGTAPRLLIYSNNQRPS
GVPDRFSGSKSGTSASLAISGLRSEDEADYYCTSWDDSLNAWVFGGGTRLTVLGQPK
AAPSVTLFPPSSEELQANKATLVCLISDFYPGAVTVAWKADSSPVKAGVETTTPSKQ
SNNKYAASSYLSLTPEQWKSHRSYSCQVTHEGSTVEKTVVPAECS MAB321 LC amino acid sequence (SEQ ID NO: 35)
DIVLTQSPPSLSASVGDRVTITCRASQSINNYLNWYQQKPGNAPRILIYGASSLVSG
VPSRFSGSGSGTDFTLTISSLQPEDFATYYCQQSYRPLYTFGPGTQLDVKRTVAAPS
VFIFPPSDEQLKSGTASVVCLLNNFYPREAKVQWKVDNALQSGNSQESVTEDSKDST
YSLSSTLTLSKADYEKHKVYACEVTHQGLSSPVTKSFNRGEC MAB322 LC amino acid sequence (SEQ ID NO: 36)
DIVMTQSPSSLSASVGDRVTITCRASESISAYLNWYQHTPGRAPKLLIYAASSLETG
VPSRFSGSGSGTEFTLTISGLQPEDFVTYYCQQTYNTPRTFGQGTKVEIKRTVAAPS
VFIFPPSDEQLKSGTASVVCLLNNFYPREAKVQWKVDNALQSGNSQESVTEDSKDST
YSLSSTLTLSKADYEKHKVYACEVTHQGLSSPVTKSFNRGEC MAB375 LC amino acid sequence (SEQ ID NO: 37)
DIQMTQSPSFLSASVGDRVTFTCRASQGIASSLAWYQQKAGKAPKLLIYAASTLEDG
VPSRFSGSGFGTEFTLTITSLQPEDFATYYCHQVNSYPRTFGPGTTVDINR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC MAB376 LC amino acid sequence (SEQ ID NO: 38)
DIQMTQSPSTLSASVGDTVTITCRASQSISTWLAWFQQKPGRAPKLLIYQASSLEGG
VPSRFSGSGSGTDFNLTISGLQPDDFATYYCLQYNTYSKSFGQGTKVEIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC MAB377 LC amino acid sequence (SEQ ID NO: 39)
DIQMTQSPSFLSASVGDRVTITCRASQGIATSLAWYQQKPGKAPRLL IYAASTLESG
VPSRFSGGGSGTDFTLTISSLQPEDFAVYYCQQVNSYPRTFGPGTKLDVKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

SEQUENCE LISTING

MAB378 LC amino acid sequence (SEQ ID NO: 40)
DIQMTQSPSFLSASVGDRVTMTCRASQGISSYLAWYQQKPGKAPKLLIYAASTLESG
VPSRFSGSGSGTEFTLTISSLQPEDFAIYYCQQVNGYPRTFGPGTKVDIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC Human IgG1 HC nucleotide sequence of constant region (introns are underlined)
(SEQ ID NO: 41)
GCCTCCACCAAGGGCCCATCAGTCTTCCCCCTGGCACCCTCTACCAAGAGCACCTCT
GGGGGCACAACGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTG
GGCACCCAGACCTACATCTGCAACGTGAATCACAAGCCCAGCAACACCAAGGTGGAC
AAGAGAGTTGGTGAGAGGCCAGCACAGGGAGGGAGGGTGTCTGCTGGAAGCCAGGCT
CAGCGCTCCTGCCTGGACGCATCCCGGCTATGCAGTCCCAGTCCAGGGCAGCAAGGC
AGGCCCCGTCTGCCTCTTCACCCGGAGGCCTCTGCCCGCCCCACTCATGCTCAGGGA
GAGGGTCTTCTGGCTTTTTCCCCAGGCTCTGGGCAGGCACAGGCTAGGTGCCCCTAA
CCCAGGCCCTGCACACAAAGGGGCAGGTGCTGGGCTCAGACCTGCCAAGAGCCATAT
CCGGGAGGACCCTGCCCCTGACCTAAGCCCACCCCAAAGGCCAAACTCTCCACTCCC
TCAGCTCGGACACCTTCTCTCCTCCCAGATTCCAGTAACTCCCAATCTTCTCTCTGC
AGAGCCCAAATCTTGTGACAAAACTCACACATGCCCACCGTGCCCAGGTAAGCCAGC
CCAGGCCTCGCCCTCCAGCTCAAGGCGGGACAGGTGCCCTAGAGTAGCCTGCATCCA
GGGACAGGCCCCAGCCGGGTGCTGACACGTCCACCTCCATCTCTTCCTCAGCACCTG
AACTCCTGGGGGGACCGTCAGTCTTCCTCTTCCCCCCAAAACCCAAGGACACCCTCA
TGATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGACAA
AGCCGCGGGAGGAGCAGTACAACAGCACGTACCGTGTGGTCAGCGTCCTCACCGTCC
TGCACCAGGACTGGCTGAATGGCAAGGAGTACAAGTGCAAGGTCTCCAACAAAGCCC
TCCCAGCCCCCATCGAGAAAACCATCTCCAAAGCCAAAGGTGGGACCCGTGGGGTGC
GAGGGCCACATGGACAGAGGCCGGCTCGGCCCACCCTCTGCCCTGAGAGTGACCGCT
GTACCAACCTCTGTCCCTACAGGGCAGCCCCGAGAACCACAGGTGTACACCCTGCCC
CCATCCCGGGAGGAGATGACCAAGAACCAGGTCAGCCTGACCTGCCTGGTCAAAGGC
TTCTATCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTATAGCAAG
CTCACCGTGGACAAGAGCAGGTGGCAGCAGGGGAACGTCTTCTCATGCTCCGTGATG
CATGAGGCTCTGCACAACCACTACACGCAGAAGAGCCTCTCCCTGTCCCCGGGTAAA
TGA MAB1 HC variable domain nucleotide sequence (SEQ ID NO: 42)
CAGGTGCAGCTGCAGGAGTCGGGCCCAGGACTGGTGAAGCCTTCGGAGACCCTGTCC
CTCATCTGCAGAGTCTCTGGTGGCTCGATCAGTAGTCATTACTGGAGCTGGATCCGG
CAGCCCCCAGGGAAGGGACTGGAGTGGATTGGATATATTTCTTATAGGGGGAAGAGC
AACCACAATCCTTCCCTTGGGAGACGAGTCTCTATGTCAATAGACACGTCGGAGAAC
CAGTTCTCCCTGAACCTGAGCTCTGTGATCGCTGCGGACACGGCCGTATATTACTGT
GCGAGAGATGCTACTGGGATCAGAGAAATCAATGCTCTTGATATCTGGGGCCAAGGG
ACAACGGTCACCGTCTCTTCA MAB8 HC variable domain nucleotide sequence (SEQ ID NO: 43)
GAGGTGCAGCTGGTGGAGTCTGGGGGAGGCCTGGTCAAGCCTGGGGGGTCCCTGAGA
CTCTCCTGTGCAGCCTCTGGTTTCACTTTCAGTACCTATACTATGAGTTGGGTCCGC
CAGGCTCCAGGGCAGGGGCTAGAGTGGGTCTCGTCCATTACTAGGACTAGTAGTAAT
ATATACTACGCAGACTCAGTGGAGGGCCGATTCACCATCTCCAGAGACAACGCCAAG
AACTCACTGTATCTGCAGATGCATAGCCTGAGAGTCGAAGACACGGCTGTGTATTAC
TGTGCGAGAATCAGCGGGGTAGTGGGACCTGTCCCCTTTGACTACTGGGGCCAGGGA
ACCCTGATCACCGTCTCCTCT MAB30 HC variable domain nucleotide sequence (SEQ ID NO: 44)
GAGGTGCAGCTGGTGGAGTCTGGGGGAGGCTTGGTCAGCCTGGAGGGTCCCTGAGA
CTCTCCTGTGCAGCCTCTGGATTCACCTTCAGTGACCACTACATGGACTGGGTCCGC
CAGGCTCCAGGGAAGGGGCTGGAGTGGGTTGGCCGTATTAGAAATAAAGCTGCCATT
TACACCACAGAATACGCCGCGTCTGTGAAAGGCAGATTCACCATCTCAAGAGATGAT
TTAAAGAGCTCAGTGTATCTGCAAATGAACAGTCTGAAAACCGACGACACGGCCATA
TATTACTGTGCTAGGAGCTATGGATACTTTGACTACTGGGGCCAGGGAACCCTGGTC
ACCGTCTCCTCA MAB42 HC variable domain nucleotide sequence (SEQ ID NO: 45)
CAGGTGCAGCTGGTACAGTCTGGGGCTGAGGTGAAGAAGCCTGGGGCCTCAGTGAAG
GTCTCCTGCAAGGCTTCTGGATATTCCTTCAACGGCTACTATATGCACTGGGTGCGA
CAGGCCCCTGGACAAGGGCTTGAGTGGATGGGTTGGATCAACCTGAGCAGTGGTGGC
ACAGATTATGCACAGAAATTTCAGGGGTGGGTCACTTTGACCAGGGACACGTCCATC
ACCACAGCCTACATGGAGTTGAGCAGCCTGAGATCGAACGACACGGCCGTGTATTAC
TGTGCGAGAATTAGACCTCGCACTGGTGGACTTGACTCCTGGGGCCAGGGAACCCTG
GTCATCGTCTCCTCA

SEQUENCE LISTING

MAB48 HC variable domain nucleotide sequence (SEQ ID NO: 46)
CAGGTGCAGCTGGTGCAGTCTGGGGCTGAGGTGAAGAAGCCTGGGTCCTCGGTGAAA
GTCTCCTGCAAGGCTTCTGGAGTCACCTTCACCGCCTATGCTATCAGTTGGGTGCGA
CAGGCCCCTGGACGAGGGCTTGAGTGGATGGAGGGATCAGCCCTTTGTTTGGAATA
GTAAATTTCGGACAGAACTTCCAGGGCAGAGTCACGATTACCGCGGACAAATCCACG
GGCGCAGCCTACATGGAGCTGAGCAGCCTGAGCTCTGAGGACACGGCCATGTATTAC
TGTGCGAGAGGACCCTATTATTACGATAGAAGTCACCTAGACTACTGGGGCCAGGGA
ACCCTGGTCACCGTCTCCTCA MAB49 HC variable domain nucleotide sequence (SEQ ID NO: 47)
CAGGTGCAGCTGGTGCAGTCTGGGGCTGAGGTGAAGAGGCCTGGGTCCTCGGTGAAG
GTCTCCTGCAAGGCTTCTGGAGGCACCTTCAGCAGTTATGCTATTAGCTGGGTGCGA
CAGGCCCCTGGACAAGGGCTTGAGTGGATGGGAGGGATCATCGGTATGTTTGGAACA
ACAAACTACGCACAGAAGTTCCAGGGCAGAGTCACGATTACCGCGGACGAATTCACG
AGCACAGCCTACATGGAGCTGACCAGCCTGAGATCTGACGACACGGCCATGTATTAC
TGTGCGAGAGACCGAAATTACTATGCTTCGGGGACTTATGACCACTGGGGCCAGGGA
ACCCTGGTCACCGTCTCCTCA MAB52 HC variable domain nucleotide sequence (SEQ ID NO: 48)
CAAGTGCTGCTGGTGCAGTCTGGGGCTGAAGTGAAGAAGCCTGGGTCCTCGGTGAAT
ATCTCTTGCAAGGCTTCTGGAGGCACTTTCAGCAACTATGCTATCTCCTGGGTGCGA
CAGGCCCCTGGACAAGGTCTTGACTGGATGGGAAGGATCATCCCTATCTTTGGAACA
GCAAACTACGCACAGAAATTCCAGGGCAGACTCACCATTACCGCGGACGAATCCACG
AGCACAGCCTACATGGAACTGAGCAGCCTGAGATCTGAAGACACGGCCGTGTTTTAC
TGTGCGATTACTAAACCGGGGTCTGTCTACGCTTTGGACGTCTGGGGCCAAGGGACC
ACGGTCACCGTCTCCTCA MAB53 HC variable domain nucleotide sequence (SEQ ID NO: 49)
CAGGTGCAGCTGGTGCAGTCTGGGGCTGAGGTGAGGAAGCCGGGGTCCTCGGTGAAG
GTCTCCTGCAAGGTTTCTGGAGGCATCATTAGGAAATATGCTATCAACTGGGTGCGA
CAGGCCCCCGGACAAGGGCTTGAGTGGATGGGAGGGATCATCGCTATCTTTAATACA
GCAAACTATGCACAGAAATTCCAGGGCAGAGTCACGATTACCGCGGACGAGTCCACG
AGCACAGTCTACATGGAGCTGAGCAGCCTGAGATCTGAAGACACGGCCCTTTATTAC
TGTGCGAGAGGAATGAATTACTACAGTGACTACTTTGACTACTGGGGCCAGGGAAGC
CTTGTCACCGTCTCCCCA MAB285 HC variable domain nucleotide sequence (SEQ ID NO: 50)
CAGGTGCAGCTGGTGCAGTCTGGGGCTGAGGTGAAGAAGCCTGGGGCCTCAGTGAAG
GTCTCCTGCCGGGCTTCTGGATACACCTTCACCGGCTACTATATGCAGTGGGTGCGG
CAGGCCCCTGGCCAAGGGCTTGAGTGGATGGGATTCATCAATGCTAACACTGGTGTC
ACAAACTTTGCTCAGAAGTTTCAGGGCAGGGTCACCTTGACCAGGGACACGTCCATC
AGCACAGCCTACATGGAGCTGAGGAGGCTGACATCTGCCGACACGGCCGTGTATTAC
TGTGCGAGAGCGCCCCAGTGGTTATCGTATTCTTTTGATATCTGGGGCCAAGGGACA
ATGGTCACCGTCTCCTCA MAB321 HC variable domain nucleotide sequence (SEQ ID NO: 51)
GAGGTGCAGCTGGTGGAGTCTGGGGCTGAGGTGAGGAGCCCTGGGGCCTCAGTGAAG
CTCTCCTGCAAGGCTTCTGCATACACCTTCATCAACTACTATCTGCACTGGGTGCGA
CAGGCCCCTGGACAAAGGCTTGAGTGGATGGGATGGATCAACCCTGACAGTGGTGTC
ACAGAATATGCACAGACATTTCAGGGCAGGGTCACCATGACCAGGGACACGTCCATC
AATACAGCCTACCTGGACCTGGAGAGACTGACATCTGACGACACGGCCGTATATTAC
TGTGCGAGAGGTTTTATTCCTTGGGGTGGGAAGTACTTCTACCTTGACTACTGGGGC
CAGGGAACCCTGGTCACCGTCTCCTCA MAB322 HC variable domain nucleotide sequence (SEQ ID NO: 52)
CAGGTACAGCTGCAGCAGTCAGGGCCAGGACTGGTGAAGCCTTCACAGACCCTGTCC
CTCACCTGCAGTGTATCTGGTAGTTTCATCAGAAGTGGAGATTATAATTGGAGTTGG
ATCCGCCAGCCCCCAGGGAAGGGCCTGGAGTGGATTGGGTACATCGATAATAGCGGG
AGCACCCACTACAACCCGTCCCTCAAGAGTCGAGTTAGCATATCAGTGGACACGTCC
AAGAACCACTTGTCCCTGAAGCTGAGTTTTGTGACTGACGCAGACACGGGCGTGTAT
TACTGTGCCGGAGAACAAGCGTCTGATAGTCGTGGTAATTACTACTACTACGCTATG
GACGTCTGGGGCCAAGGGACCCCGGTCACCGTCTCCTCA MAB375 HC variable domain nucleotide sequence (SEQ ID NO: 53)
CAGGTGCAGCTGCAGCAGTCGGGCCCCGGACTGATGAAGCCTTCGGAGACCCTGTCC
CTCAGCTGCACTGTCTCTGGTGACTCCGTCAGTAGTTTTTATTGGAGTTGGATTCGG
CAGTCTCCAGGAAAGGGACTGGAGTGGATTGGGTATTTGCTTTACAGTGGGAATACC
AAGTATAATCCGTCCCTCAAGAGTCGAGCCACCATATCAAGAGACACGTCCAAGAAC
CAGTTGTCCCTGGAGTTGACCTCTCTGACCGCTGCGGACACGGCCGTCTACTATTGT
GCGAGAGTGGTGAGATGGCGACATGGTGGCGATTTGGACGTCTGGGGCCAAGGGACC
ACGGTCACCGTCTCCTCA MAB376 HC variable domain nucleotide sequence (SEQ ID NO: 54)
CAGGTGCAGCTGGTGCAGTCCGGGGGGGACTTGGTCCAGCCGGGGGGTCCCTGAGA
CTGTCATGTGCAGTCTCTGGATTCATCTTTAGAAAATATATCATGAGTTGGGTCCGG
CAGGCTCCAGGGAAGGGGCCGGAGTGGGTCGCAGTTATTAGTTCTAGTGGTGACCGG
ACATTCTACGCCGACTCCGTGGAGGGCCGCTTCATCGTCTCCAGAGACAATTCCAAG GACACACTGTTTCTGCAAATGAACAGCCTGAGAACCGAGGACACGGCCATGTATTAC
TGTGCGAAAGACCTTTTGGGATTTTGTAGTGGTGGTGATTGCCTGAAGGTCTTCGAT
CTCTGGGGCCGAGGCACCATGGTCACTGTCTCCTCA MAB377 HC variable domain nucleotide sequence (SEQ ID NO: 55)
CAGGTGCAGCTGCTGCAGTCGGGCCCAGGACTGATAAAGGCTTCGGAGACCCTGTCT
CTCAGCTGCAGTGTCTCTAATGACTCCGTCAGTAATTATTATTGGAGTTGGATCCGG
CAGTCCCCAGAGAAGGGACTGGAGTGGATTGGGTATTTGCTTTATAGTGGGAATACC
AAGTACAATCCCTCCCTCAAGAGTCGAGCCATCATATCAAGAGACATGTCCAAAAAT
CAGTTGTCCCTCAGAGTGACTTCTGTGACCGCTGCGGACACGGCCATATATTATTGT
GCGCGAGTGGTGAGATGGCGATTTGGTGGTGATATGGACGTCTGGGGTCAAGGGACC
GCGGTCACCGTCTCCACA MAB378 HC variable domain nucleotide sequence (SEQ ID NO: 56)
CAGGTGCAGCTGCAGCAGTCGGGCCCAGGACTGATAAAGCCTTCGGAGACCCTGTCT
CTCAGCTGCTCTGTCTCTGGTGACTCCGTCAATAATTATTATTGGAGTTGGATCCGG
CAGCCCCCAGAGAAGGGACTGGAGTGGATTGGGTATCTGCAGTATAGTGGGAGTACA
AAGTACAACCCCTCCCTCAAGAGTCGAGTCACCATATCAAGAGACACGTCCAAAAAC
CAGTTGTCCCTGAAGCTGACCTCTGTGACCGCTGCGGACACGGCCATATATTATTGT
GCGAGAGTGGTGAGATGGCGACATGGTGGGGATATGGACGTCTGGGGCCAAGGGACC
GCGGTCACCGTCTCCTCT Human LC nucleotide sequence of constant kappa region (SEQ ID NO: 57)
CGAACTGTGGCTGCACCATCTGTCTTCATCTTCCCGCCATCTGATGAGCAGTTGAAA
TCTGGAACTGCTAGCGTTGTGTGCCTGCTGAATAACTTCTATCCCAGAGAGGCCAAA
GTACAGTGGAAGGTGGATAACGCCCTCCAATCGGGTAACTCCCAGGAGAGTGTCACA
GAGCAGGACAGCAAGGACAGCACCTACAGCCTCAGCAGCACCCTGACGCTGAGCAAA
GCAGACTACGAGAAACACAAAGTCTACGCCTGCGAAGTCACCCATCAGGGCCTGAGC
TCGCCCGTCACAAAGAGCTTCAACAGGGGAGAGTGTTAG Human LC nucleotide sequence of constant lambda region (SEQ ID NO: 58)
GGTCAGCCCAAGGCTGCCCCCTCTGTCACTCTGTTCCCGCCCTCTAGCGAGGAGCTT
CAAGCCAACAAGGCCACACTGGTGTGTCTCATAAGTGACTTCTACCCGGGAGCCGTG
ACAGTGGCCTGGAAGGCAGATAGCAGCCCCGTCAAGGCGGGAGTGGAGACCACCACA
CCCTCCAAACAAAGCAACAACAAGTACGCGGCCAGCAGCTATCTGAGCCTGACGCCT
GAGCAGTGGAAGTCCCACAGAAGCTACAGCTGCCAGGTCACGCATGAAGGGAGCACC
GTGGAGAAGACAGTGGTCCCTGCAGAATGCTCT MAB1 LC variable domain nucleotide sequence (SEQ ID NO: 59)
GACATCCAGATGACCCAGTCTCCATCCTCCCTGTCTGCATCTGGAGGAGACAGAGTC
ACCATCACTTGCCGGGCAAGTCAGAGTGTTAGTACGTATTTAAATTGGTATCAGCAG
AAACCAGGGAAAGCCCCTAACCTCCTGGTCTATGCTGTATCCAATTTACAACGTGGC
GTGCCATCAAGGTTCAGTGGCAGTGGATCTGGGACACATTTCACTCTCACAATCAGC
AGTCTGCAACCTGAGGATTTCGCAACTTACTACTGTCAACAGAGTTACAGTGACCCT
CTCACTTTCGGCGGAGGGACCAAGGTGGAGATCAAA MAB8 LC variable domain nucleotide sequence (SEQ ID NO: 60)
GACATCCAGATGACCCAGTCTCCATCTTCCCTGTCTGCATCTGTAGGAGACAGAGTC
ACCATCACTTGCCGGGCAAGTCAGACCATTAGCAAGTATTTAAATTGGTATCAGCAG
AAGCCAGGGAGAGCCCCTAAACTCCTGATCTACTCTGCGTCCAGTTTGCAAAGTGGG
GTCCCATCAAGGTTCACTGGCAGTGGATCTGGGACAGATTTCACTCTCACCATCACC
AGTCTGCAACCTGAAGATTTTGCAACTTACTACTGTCAACAGAGTTACAGACCCTCC
CAGATCACTTTCGGCCCTGGGACCAAAGTGGATATCAAA MAB30 LC variable domain nucleotide sequence (SEQ ID NO: 61)
GACATCCAGATGACCCAGTCTCCTTCCACCCTGTCTGCATCTGTAGGAGACAGAGTC
ACCATCACTTGCCGGGCCAGTCAGAGTATTAGTAGTTGGTTGGCCTGGTATCAGCAG
AAACCAGGGAACGCCCCTAACCTCCTGATCTATAAGGCGTCTAGTTTAGAAAGTGGG
GTCCCATCAAGGTTCAGCGGCAGTGGATCTGGGACAGAATTCACTCTCACCATCAGC
AGCCTGCAGCCTGATGATTTTGCAACTTATTACTGCCAACAGTATGATACTTATTCT
CCGACGTTCGGCCAAGGGACCAAGGTGGAAATCAAA MAB42 LC variable domain nucleotide sequence (SEQ ID NO: 62)
CAGTCTGCCCTGACTCAGCCTGCCTCCGGGTCTGGGTCTGCTGGACAGGCGATCACC
ATCTCCTGCACTGGAACCGGCACTGACGTCTGTGCTTATAACTTTGTCTCCTGGTAC
CAACACCACCCCGGCGAAGCCCCCAAACTCATGATTTATGATGTCGATAATCGGCCC
TCATGGGTTTCTAATCGCTTCTCTGGCTCCAAGTCTGGTAACACGGCCTCCCTGACC
ATCTCTGGGCTCCAGGCTGAGGACGAGGCTGATTACTACTGCAGCTCATATAGAAGG
AACGGCCCTTGCTTGTTCGGCGGAGGGACCAAGCTGACCGTCCTG MAB48 LC variable domain nucleotide sequence (SEQ ID NO: 63)
GAAATTGTGTTGACGCAGTCTCCAGGCACCCTGTCTTTGTCTCCAGGGGAAAGAGCC
ACCCTCTCCTGCAGGGCCAGTCAGAGTGTTGGCAGCAGCGACTTAGCCTGGTACCAG
CAGAAACCTGGCCAGGCTCCCAGGCTCCTCATATATGGTGCATCCAGCCGGGCCACT
GGCATCCCAGACAGGTTCAGTGGCAGTGGGTCTGGGACAGACTTCACTCTCACCATC
AGCAGACTGGAGCCTGAAGATTTTGCAGTGTATTACTGTCAGCAGTATGTCAGTTCA
CCCCTCACTTTCGGCGGAGGGACCAAGGTGGAGATCAAG

SEQUENCE LISTING

MAB49 LC variable domain nucleotide sequence (SEQ ID NO: 64)
GACATCCAGATGACCCAGTCTCCATCCTCCCTGTCTGCATCTGTAGGAGACAGAGTC
ACCATCACTTGCCGGGCAAGTCAGAGCATTAGCAGGTATTTAAATTGGTATCAGCAG
AAACCAGGGAAAGCCCCTAAACTCCTGATCTATTCTGCATCCAGTTTGCAAAGTGGG
GTCCCATCAAGGTTCGGTGGCAGTGGATCTGGGACAGATTTCACTCTCACCATCAGC
AGTCTGCAACCTGAAGATTTTGCACTTTACTACTGTCAACAGACTTACAGTATCCCG
ATCACCTTCGGCCAAGGGACACGACTGGACTTTAAA MAB52 LC variable domain nucleotide sequence (SEQ ID NO: 65)
GACATCCAGATGACCCAGTCTCCATCCTCCCTGTCTGCATCTGTAGGAGACAGAGTC
ACTATCACTTGCCGGGCAAGTCAGACCATTAGCACCTATTTAAATTGGTATCAGCAG
AAACCAGGGAAAGCCCCTAACCTCCTGATCTATACTGCATCCAGTTTGCAAAGCGGG
GTCCCATCAAGATTCAGTGGCAGTGGATCTGGGACAGATTTCACTCTCACCATCAGC
AGTCTGCAACCTGAAGATTTTGCAACTTATTACTGTCAACAGAGTTACGATGCCCCC
ACGTGGACCTTCGGCCCAGGGACCAAGGTGGAAATCAAA MAB53 LC variable domain nucleotide sequence (SEQ ID NO: 66)
GAAATTGTGTTGACACAGTCTCCAGGCACCCTGTCTTTGTCTCCAGGGGAAAGAGCC
ACCCTCTCCTGCAGGGCCAGTCAGAGTGTTAGAAGCAACAACTTAGCCTGGTACCAG
CACAAACCTGGCCAGGCTCCCAGGCTCCTCATCTTTGGTGCATCCAGCAGGGCCACT
GGCATCCCAGACAGGTTCAGTGGCAGTGGGTCTGGGACAGACTTCACTCTCACCATC
AGCAGACTGGAGCCTGAAGATTTTGCAGTATATTACTGTCAGCAGTATGGTAGCTCA
CCTGCGCTCACTTTCGGCGGAGGGACCAAGGTGGAGATCAAA MAB285 LC variable domain nucleotide sequence (SEQ ID NO: 67)
CAGTCTGTGCTGACTCAGCCACCCTCAGCGTCTGGGACCCCCGGGCAGAGGGTCACC
ATCTCTTGTTCTGGAAGCAGCTCCAACATCGGAAGTAATCCTGTAAACTGGTACCAG
CAGCTCCCAGGAACGGCCCCCAGACTTCTCATCTATAGTAATAATCAGCGGCCCTCA
GGGGTCCCTGACCGATTCTCTGGCTCCAAGTCTGGCACCTCAGCCTCCTGGCCATC
AGTGGGCTCCGGTCCGAGGATGAGGCTGATTACTACTGTACATCATGGGATGACAGC
CTGAATGCTTGGGTGTTCGGCGGGGGGACCAGGCTGACCGTCCTA MAB321 LC variable domain nucleotide sequence (SEQ ID NO: 68)
GATATCGTGTTGACTCAGTCTCCACCCTCCCTGTCTGCATCTGTGGGGACAGAGTC
ACCATCACTTGCCGGGCAAGTCAGAGCATTAATAACTACTTAAATTGGTATCAACAG
AAACCAGGGAACGCCCCAAGAATACTAATCTATGGTGCATCCAGTTTGGTAAGTGGG
GTCCCATCAAGGTTCAGTGGCAGTGGATCTGGGACAGATTTCACCCTCACCATCAGC
AGTCTGCAACCTGAAGATTTTGCAACTTACTACTGTCAACAGAGTTACCGGCCCCTG
TACACTTTTGGCCCGGGGACCCAGCTGGATGTCAAA MAB322 LC variable domain nucleotide sequence (SEQ ID NO: 69)
GATATCGTGATGACCCAGTCTCCATCTTCCCTGTCTGCATCTGTGGGAGACAGAGTC
ACCATCACTTGCCGGGCAAGTGAGAGCATTAGCGCTTATTTAAATTGGTATCAGCAC
ACACCAGGGAGAGCCCCTAAGCTCCTGATCTATGCTGCCTCCAGTTTGGAAACTGGG
GTCCCATCAAGGTTCAGTGGCAGTGGATCTGGCACAGAATTCACTCTCACCATCAGC
GGTCTGCAACCTGAAGATTTTGTCACTTACTACTGTCAACAGACTTACAATACCCCT
CGGACCTTCGGCCAAGGGACCAAGGTGGAAATCAAA MAB375 LC variable domain nucleotide sequence (SEQ ID NO: 70)
GATATCCAGATGACCCAGTCTCCATCCTTCTTGTCTGCATCTGTGGGAGACAGAGTC
ACCTTCACTTGCCGGGCCAGTCAGGGCATTGCCAGTTCTTTAGCCTGGTATCAGCAA
AAAGCAGGGAAAGCCCCTAAGCTCCTGATCTATGCTGCTTCTACTTTGGAAGATGGG
GTCCCATCAAGGTTCAGCGGCAGTGGATTTGGGACAGAATTCACTCTCACAATCACC
AGCCTGCAGCCTGAAGATTTTGCAACCTATTACTGTCATCAGGTGAATAGTTACCCT
CGGACTTTCGGCCCTGGGACCACAGTGGATATCAAC MAB376 LC variable domain nucleotide sequence (SEQ ID NO: 71)
GATATCCAGATGACCCAGTCTCCTTCCACCCTGTCTGCATCTGTGGGAGACAGTC
ACCATCACTTGCCGGGCCAGTCAGAGTATTAGTACTTGGTTGGCCTGGTTTCAGCAG
AAACCAGGGAGAGCCCCTAAACTCCTGATCTATCAGGCGTCTAGTTTGGAAGGTGGG
GTCCCATCAAGGTTCAGCGGCAGTGGGTCTGGGACAGACTTCAACCTCACCATCAGC
GGCCTGCAGCCTGATGATTTTGCAACTTATTACTGCCTACAATATAACACTTATTCG
AAGTCATTCGGCCAAGGGACCAAGGTGGAAATCAAAC MAB377 LC variable domain nucleotide sequence (SEQ ID NO: 72)
GATATCCAGATGACCCAGTCTCCATCCTTCTTGTCTGCATCTGTCGGAGACAGAGTC
ACCATCACCTGCCGGGCCAGTCAGGGCATTGCCACTTCTTTAGCCTGGTATCAGCAA
AAACCTGGGAAAGCCCCGAGGCTCCTGATCTATGCTGCATCCACTTTGGAAAGTGGG
GTCCCATCAAGGTTCAGCGGCGGTGGATCTGGGACAGACTTCACTCTCACAATCAGC
AGTCTGCAGCCCGAAGATTTTGCTGTTTATTACTGTCAACAGGTTAACTCCTATCCT
CGGACTTTCGGCCCTGGGACCAAACTGGATGTCAAAC MAB378 LC variable domain nucleotide sequence (SEQ ID NO: 73)
GATATCCAGATGACCCAGTCTCCATCCTTCTTGTCTGCATCTGTAGGAGACAGAGTC
ACCATGACCTGCCGGGCCAGTCAGGGCATTAGCAGTTATTAGCCTGGTATCAGCAA
AAACCAGGGAAAGCCCCTAAGCTCCTGATCTATGCTGCATCGACTTTGGAAAGTGGG

SEQUENCE LISTING

```
GTCCCATCAAGGTTCAGCGGCAGTGGATCTGGGACAGAATTCACTCTCACAATCAGC
AGCCTGCAGCCCGAAGATTTTGCAATTTATTACTGTCAACAGGTTAATGGTTACCCT
CGGACTTTCGGCCCTGGGACCAAAGTGGATATCAAAC

RGLFGAIAGFIENGW (SEQ ID NO: 74).

MAB53 Heavy Chain (SEQ ID NO: 75)
QVQLVQSGAEVRKPGSSVKVSCKVSGGIIRKYAINWVRQAPGQGLEWMGGIIAIFNT
ANYAQKFQGRVTITADESTSTVYMELSSLRSEDTALYYCARGMNYYSDYFDYWGQGS
LVTVSPASTKGPSVFPLVPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK MAB53 Light Chain (SEQ ID NO: 76)
EIVLTQSPGTLSLSPGERATLSCRASQSVRSNNLAWYQHKPGQAPRLLIFGASSRAT
GIPDRFSGSGSGTDFTLTISRLEPEDFAVYYCQQYGSSPALTFGGGTKVEIKRTVAA
PSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

GGIIRKYAIN (SEQ ID NO: 77)

GGIIAIFNTANYAQKFQG (SEQ ID NO: 78)

ARGMNYYSDYFDY (SEQ ID NO: 79)

RASQSVRSNNLA (SEQ ID NO: 80)

GASSRAT (SEQ ID NO: 81)

QQYGSSPALT (SEQ ID NO: 82)

IGHV1-69*01 (SEQ ID NO: 83)
QVQLVQSGAEVRK PGSSVKVSCKVSGGIIRKYAINWVRQAPGQG
LEWMGGIIAIFNTANYAQKFQGRVTITADESTSTVYMELSSLRSEDTALYYCARGMN
YYSDYFDYWGQGSLVTTVS

IGKV3-20*01 (SEQ ID NO: 84)
EIVLTQSPGTLSLSPGERATLSCRASQSVRSNNLAWYQHKPGQAPRLLIFGASSRAT
GIPDRFSGSGSGTDFTLTISRLEPEDFAVYYCQQYGSSPALTFGGGTKVEIK
```

The invention claimed is:

1. An isolated recombinant monoclonal antibody or an antigen binding fragment thereof that specifically binds the HA0 protein from influenza A viral clades H1, H5, H7 and H9 the monoclonal antibody or antigen binding fragment thereof comprising a heavy chain variable region comprising a CDR1 of the sequence GGIIRKYAIN (SEQ ID NO: 77), a CDR2 of the sequence GGIIAIFNTANYAQKFQG (SEQ ID NO: 78), and a CDR3 of the sequence ARGMNYYSDYFDY (SEQ ID NO: 79) and a light chain variable region comprising a CDR1 of the sequence RASQSVRSNNLA (SEQ ID NO: 80), a CDR2 of the sequence GASSRAT (SEQ ID NO: 81), and a CDR3 of the sequence QQYGSSPALT (SEQ ID NO: 82), said antibody or fragment being a single-chain antibody or fragment.

2. An isolated recombinant monoclonal antibody or an antigen binding fragment-thereof that specifically binds the HA0 and HA2 protein from influenza A viral clades H1, H5, H7 and H9; the monoclonal antibody or the antigen binding region comprising
  a heavy chain variable region comprising the sequence QVQLVQSGAEVRK PGSSVKVSCKVSGGIIRKYAINWVRQAPGQGLEWMGGIIAIFNTANYAQKFQGRVTI TADESTSTVYMELSSLRSEDTALYYCARGMNYYSDYFDYWGQGSLVTVSP (amino acids 1-120 of SEQ ID NO:75), said antibody being a single chain antibody.

3. The monoclonal antibody of claim 2, or an antigen binding fragment thereof, further comprising a light chain variable region comprising the sequence EIVLTQSPGTLSLSPGERATLSCRASQSVRSNNLAWYQHKPGQAPRLLIFGASSRA TGIP DRFSGSGSGTDFTLTISRLEPEDFAVYYCQQYGSSPALTFGGGTKVEIK (amino acids 1-109 of SEQ ID NO:76).

4. A pharmaceutical composition comprising the recombinant monoclonal antibody or antigen binding fragment thereof in accordance with claim 1 in an amount effective to confer passive immunity to a subject against influenza A viral clades H1, H5, H7 and H9 upon administration to the subject.

5. A recombinant monoclonal antibody of claim 1, or an antigen binding fragment thereof that specifically binds the HA0 protein from influenza A viral clades H1, H5, H7 and H9 the monoclonal antibody or antigen binding fragment thereof comprising
  a heavy chain variable region comprising a CDR1 of the sequence GGIIRKYAIN (SEQ ID NO: 77), a CDR2 of the sequence GGIIAIFNTANY AQKFQG (SEQ ID NO: 78), and a CDR3 of the sequence ARGMNYYSDYFDY (SEQ ID NO: 79) and
  a light chain variable region comprising a CDR1 of the sequence RASQSVRSNNLA (SEQ ID NO: 80), a CDR2 of the sequence GASSRAT (SEQ ID NO: 81), and a CDR3 of the sequence QQYGSSPALT (SEQ ID NO: 82),
  wherein the monoclonal antibody or antigen binding fragment is a bispecific antibody.

6. A pharmaceutical composition comprising the recombinant monoclonal antibody or the antigen binding fragment thereof in accordance with claim 5.

7. A pharmaceutical composition comprising the recombinant monoclonal antibody or antigen binding fragment thereof in accordance with claim 2 or 3 in an amount effective to confer passive immunity to a subject against influenza A viral clades HI, H5, H7 and H9 upon administration to the subject.

8. A monoclonal antibody or an antigen binding fragment thereof that specifically binds the HA0 and HA2 protein from influenza A viral clades H1, H5, H7 and H9, comprising
  a heavy chain variable region comprising the sequence QVQLVQSGAEVRKPGSSVKVSCKVSGGIIRKY AINWVRQAPGQGLEWMGGIIAIFNTANY AQKFQGRVTITADESTSTVYMELSS LRSEDTAL YYCARGMNYYSDYFDYWGQGSLVTVSP (amino acids 1-120 of SEQ ID NO:75), and optionally further comprising
  a light chain variable region comprising the sequence EIVLTQSPGTLSLSPGERATLSCRASQSVRSNNLAWYQHKPGQAPRLLIFGASSRA TGIPDRFSGSGSGTDFTLTISRLEPEDFAVYYCQQYGSSPALTFGGGTKVEIK (amino acids 1-109 of SEQ ID NO:76), wherein the monoclonal antibody or the antigen binding fragment thereof is a bispecific antibody.

9. A pharmaceutical composition comprising the monoclonal antibody or the antigen binding fragment thereof of claim 8.

10. A monoclonal antibody produced recombinantly by a nonhuman host cell modified to contain a nucleotide sequence encoding a heavy chain variable region comprising the sequence QVQL VQSGAEVRKPGSSVKVSCKVSGGIIRKY AINWVRQAPGQGLEWMGGIIAIFNTAN YAQKFQGRVTITADESTSTVYMELSSLRSEDTAL YYCARGMNYYSDYFDYWGQGSL VT VSP (amino acids 1-120 of SEQ ID NO:75) and a light chain variable region comprising the sequence EIVLTQSPGTLSLSPGERATLSCRASQSVRSNNLAWYQHKPGQAPRLLIFGASSRA TGIPDRFSGSGSGTDFTLTISRLEPEDFAVYYCQQYGSSPALTFGGGTKVEIK (amino acids 1-109 of SEQ ID NO:76) operably linked to control sequences for expression, said antibody specifically binding to the HA0 protein from influenza A viral clades H1, H5, H7 and H9.

11. A monoclonal antibody produced recombinantly by a nonhuman host cell modified to contain a nucleotide sequence encoding a heavy chain variable region comprising a CDR1 of the sequence GGIIRKYAIN (SEQ ID NO: 77), a CDR2 of the sequence GGIIAIFNT ANY AQKFQG (SEQ ID NO: 78), and a CDR3 of the sequence ARGMNYYSDYFDY (SEQ ID NO: 79) and a light chain variable region comprising a CDR1 of the sequence RASQSVRSNNLA (SEQ ID NO: 80), a CDR2 of the sequence GASSRAT (SEQ ID NO: 81), and a CDR3 of the sequence QQYGSSPALT (SEQ ID NO: 82), aid nucleotide sequence operably linked to control sequences for expression, said antibody, specifically binding to the HA0 protein from influenza A viral clades H1, H5, H7 and H9.

12. An antibody or fragment thereof according to claim 1 wherein the fragment is selected from the group consisting of an Fab fragment, a F(ab')2' fragment and an Fv fragment.

13. An antibody or fragment thereof according to claim 2 wherein the fragment is selected from the group consisting of an Fab fragment, a F(ab')2' fragment and an Fv fragment.

14. A pharmaceutical composition comprising the recombinant monoclonal antibody or antigen binding fragment thereof in accordance with claim 1.

15. A method for the treatment or prophylaxis of influenza infection in a subject at risk of infection by influenza A or exposed to or infected with influenza A which method comprises administering to the subject an effective amount for conferring passive immunity to said subject against influenza A viral clades H1, H5, H7 and H9 of the composition of claim 14 or 5.

* * * * *